(12) United States Patent
Hess et al.

(10) Patent No.: US 8,974,504 B2
(45) Date of Patent: Mar. 10, 2015

(54) DYNAMIC BONE FRACTURE PLATES

(71) Applicant: Spinal Simplicity LLC, Lenexa, KS (US)

(72) Inventors: Harold Hess, Leawood, KS (US); Melissa Frock, Larwill, IN (US); Adam Frock, Larwell, IN (US); Adam Rogers, Norfolk, VA (US); Todd Moseley, Olathe, KS (US); Jonathan Hess, Kansas City, MO (US); Paul Sand, Redwood City, CA (US); Carlos Gonzalez, Kansas City, MO (US)

(73) Assignee: Spinal Simplicity LLC, Lenexa, KS (US)

( * ) Notice: Subject to any disclaimer, the term of this patent is extended or adjusted under 35 U.S.C. 154(b) by 0 days.

(21) Appl. No.: 13/891,839

(22) Filed: May 10, 2013

(65) Prior Publication Data

US 2013/0304067 A1 Nov. 14, 2013

Related U.S. Application Data

(63) Continuation-in-part of application No. 13/586,083, filed on Aug. 15, 2012, now Pat. No. 8,574,270.

(60) Provisional application No. 61/688,247, filed on May 10, 2012, provisional application No. 61/704,863, filed on Sep. 24, 2012, provisional application No. 61/803,678, filed on Mar. 20, 2013.

(51) Int. Cl.
*A61B 17/66* (2006.01)
*A61B 17/80* (2006.01)
(Continued)

(52) U.S. Cl.
CPC ......... *A61B 17/8004* (2013.01); *A61B 17/7059* (2013.01); *A61B 17/8042* (2013.01);
(Continued)

(58) Field of Classification Search
USPC .............. 606/70–71, 280–286, 293–294, 606/902–906
See application file for complete search history.

(56) References Cited

U.S. PATENT DOCUMENTS

| 4,269,180 A | 5/1981 | Dall et al. |
| 4,998,936 A | 3/1991 | Mehdian et al. |

(Continued)

FOREIGN PATENT DOCUMENTS

| DE | 3412769 A1 | 10/1985 |
| EP | 1 169 971 A2 | 1/2002 |

(Continued)

OTHER PUBLICATIONS

Synthes (Copyright) Spine, Vectra-T (Trademark), Anterior Cervical Plating System, "Technique Guide," 2006.
(Continued)

*Primary Examiner* — Sameh Boles
(74) *Attorney, Agent, or Firm* — Locke Lord LLP; Scott D. Wofsy; George N. Chacias

(57) ABSTRACT

A bone fracture plate assembly including female and male plate portions. The female plate portion has a post, a female dovetail, and an extending arm with a group of ratchet teeth. The male plate portion has two upstanding posts, a male dovetail for coupling to the female dovetail so that the plate portions move linearly with respect to each other, a slot for the arm, and a pawl for engaging the ratchet teeth. A spring, coupled to the posts of the plate portions, dynamically connects the plate portions by applying a compressive load therebetween. The spring has a pair of elongated ears, each defining a slot to allow for relative movement of the plate portions. The ratchet teeth are engaged by the pawl to retain the plate portions together, and the spring mounts on the posts of the plate portions such that the spring biases the plate portions together.

13 Claims, 20 Drawing Sheets

(51) Int. Cl.
*A61B 17/70* (2006.01)
*A61B 17/88* (2006.01)

(52) U.S. Cl.
CPC ......... *A61B17/8047* (2013.01); *A61B 17/8009* (2013.01); *A61B 17/8028* (2013.01); *A61B 17/8875* (2013.01)
USPC ....................................................... 606/282

(56) References Cited

U.S. PATENT DOCUMENTS

| | | | |
|---|---|---|---|
| 5,180,381 A | 1/1993 | Aust et al. | |
| 5,201,735 A | 4/1993 | Chapman et al. | |
| 5,209,756 A | 5/1993 | Seedhom et al. | |
| 5,330,477 A | 7/1994 | Crook | |
| 5,364,399 A | 11/1994 | Lowery et al. | |
| 5,531,554 A | 7/1996 | Jeanson et al. | |
| 5,558,674 A | 9/1996 | Heggeness et al. | |
| 5,578,034 A | 11/1996 | Estes | |
| 5,603,713 A | 2/1997 | Aust et al. | |
| 5,735,853 A | 4/1998 | Olerud | |
| 5,836,948 A | 11/1998 | Zucherman et al. | |
| 5,876,402 A | 3/1999 | Errico et al. | |
| 5,941,881 A | 8/1999 | Barnes | |
| 6,017,345 A | 1/2000 | Richelsoph | |
| 6,066,141 A | 5/2000 | Dall et al. | |
| 6,093,201 A | 7/2000 | Cooper et al. | |
| 6,152,927 A | 11/2000 | Farris et al. | |
| 6,193,721 B1 | 2/2001 | Michelson | |
| 6,224,602 B1 | 5/2001 | Hayes | |
| 6,258,089 B1 | 7/2001 | Campbell et al. | |
| 6,261,291 B1 | 7/2001 | Talaber et al. | |
| 6,293,949 B1 | 9/2001 | Justis et al. | |
| D449,692 S | 10/2001 | Michelson | |
| 6,331,179 B1 | 12/2001 | Freid et al. | |
| 6,336,930 B1 | 1/2002 | Stalcup et al. | |
| 6,402,756 B1 | 6/2002 | Ralph et al. | |
| 6,413,259 B1 | 7/2002 | Lyons et al. | |
| 6,599,290 B2 | 7/2003 | Bailey et al. | |
| 6,626,907 B2 | 9/2003 | Campbell et al. | |
| 6,626,944 B1 | 9/2003 | Taylor | |
| 6,669,700 B1 | 12/2003 | Farris et al. | |
| 6,730,127 B2 | 5/2004 | Michelson | |
| 6,936,050 B2 | 8/2005 | Michelson | |
| 6,945,973 B2 | 9/2005 | Bray | |
| 6,949,123 B2 | 9/2005 | Reiley | |
| 7,001,387 B2 | 2/2006 | Farris et al. | |
| 7,033,377 B2 | 4/2006 | Miller, III | |
| 7,229,444 B2 | 6/2007 | Boyd | |
| 7,255,698 B2 | 8/2007 | Michelson | |
| 7,273,481 B2 | 9/2007 | Lombardo et al. | |
| 7,276,070 B2 | 10/2007 | Muckter | |
| D602,589 S | 10/2009 | Bush, Jr. | |
| 7,601,170 B2 | 10/2009 | Winslow et al. | |
| D603,964 S | 11/2009 | Kriska et al. | |
| 7,611,527 B2 | 11/2009 | Freid et al. | |
| 7,618,439 B2 | 11/2009 | Zubok et al. | |
| 7,625,378 B2 | 12/2009 | Foley | |
| 7,635,366 B2 | 12/2009 | Abdou | |
| 7,651,517 B2 | 1/2010 | Konieczynski et al. | |
| 7,749,256 B2 | 7/2010 | Farris et al. | |
| 7,887,547 B2 | 2/2011 | Campbell et al. | |
| 8,262,711 B2 | 9/2012 | Hess | |
| 2003/0130661 A1 | 7/2003 | Osman | |
| 2003/0208204 A1 | 11/2003 | Bailey | |
| 2004/0133205 A1 | 7/2004 | Thramann et al. | |
| 2004/0220571 A1 | 11/2004 | Assaker | |
| 2005/0010215 A1 | 1/2005 | Delecrin | |
| 2005/0010227 A1 | 1/2005 | Paul | |
| 2005/0043732 A1* | 2/2005 | Dalton | 606/61 |
| 2005/0065521 A1 | 3/2005 | Steger | |
| 2005/0137597 A1 | 6/2005 | Butler et al. | |
| 2005/0149026 A1 | 7/2005 | Butler | |
| 2005/0149027 A1 | 7/2005 | Campbell et al. | |
| 2005/0251138 A1 | 11/2005 | Boris et al. | |
| 2005/0261690 A1 | 11/2005 | Binder et al. | |
| 2005/0283152 A1 | 12/2005 | Lindemann | |
| 2006/0030852 A1 | 2/2006 | Sevrain | |
| 2006/0084985 A1 | 4/2006 | Kim | |
| 2006/0155285 A1 | 7/2006 | Anderson | |
| 2007/0073297 A1 | 3/2007 | Reynolds | |
| 2007/0213729 A1 | 9/2007 | Lindemann et al. | |
| 2008/0033448 A1 | 2/2008 | Robinson | |
| 2009/0012571 A1 | 1/2009 | Perrow et al. | |
| 2009/0254185 A1 | 10/2009 | Dollinger | |
| 2010/0016901 A1 | 1/2010 | Robinson | |
| 2010/0234895 A1 | 9/2010 | Hess | |

FOREIGN PATENT DOCUMENTS

| | | |
|---|---|---|
| WO | 00/78238 A1 | 12/2000 |
| WO | 02/24086 A1 | 3/2002 |
| WO | 2005/006997 A1 | 1/2005 |
| WO | 2006/104487 A1 | 10/2006 |
| WO | 2006/119242 A1 | 11/2006 |
| WO | 2007/117571 A2 | 10/2007 |
| WO | 2008/005380 A2 | 1/2008 |

OTHER PUBLICATIONS

Medtronic, Atlantic Translational (Trademark) Anterior Cervical Plate System Surgical Technique, Product Information, Todd C. Bonvallet, et al., 2008.

Written Opinion of the International Searching Authority, mailed Aug. 9, 2013, in corresponding PCT application PCT/US2013/040570.

* cited by examiner

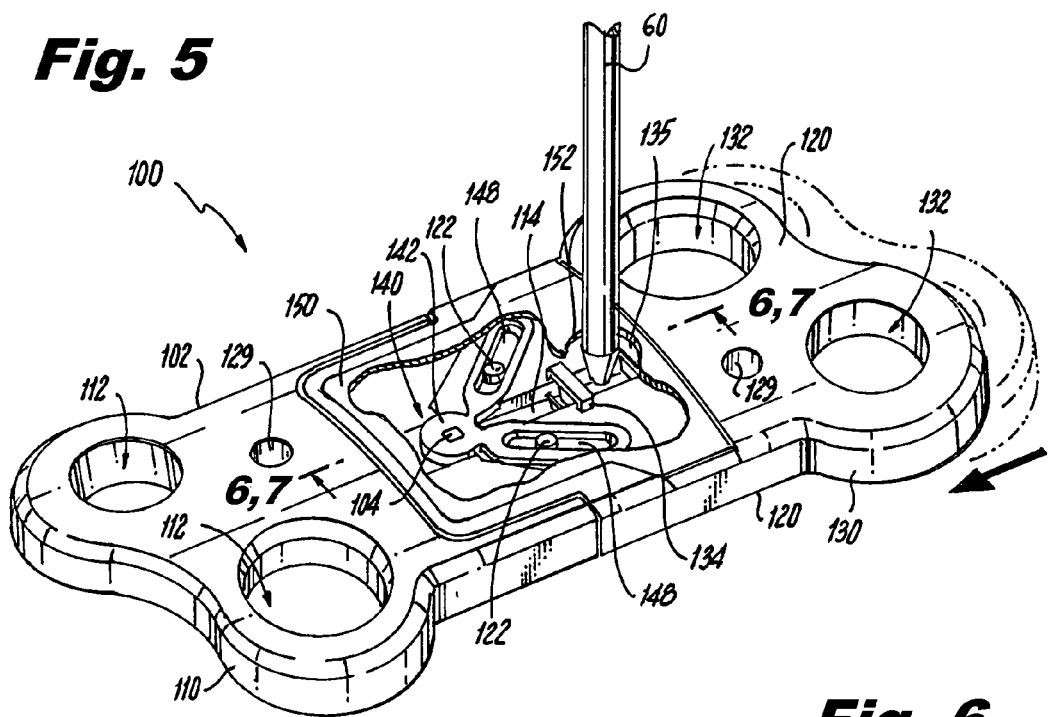
*Fig. 5*
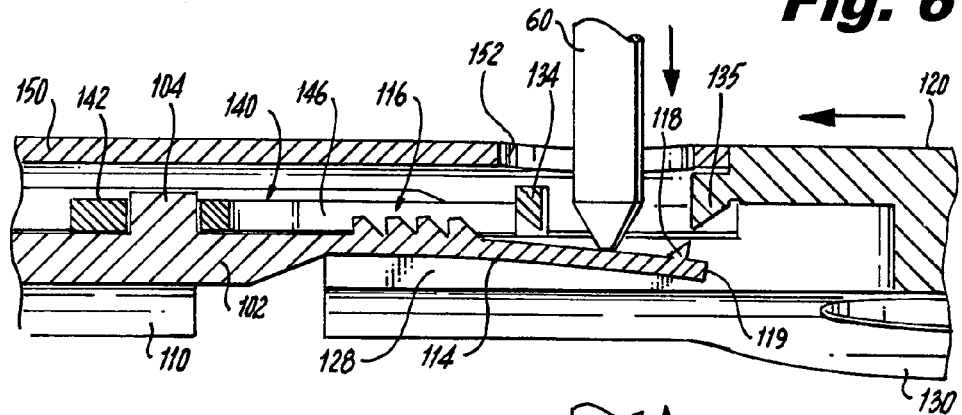
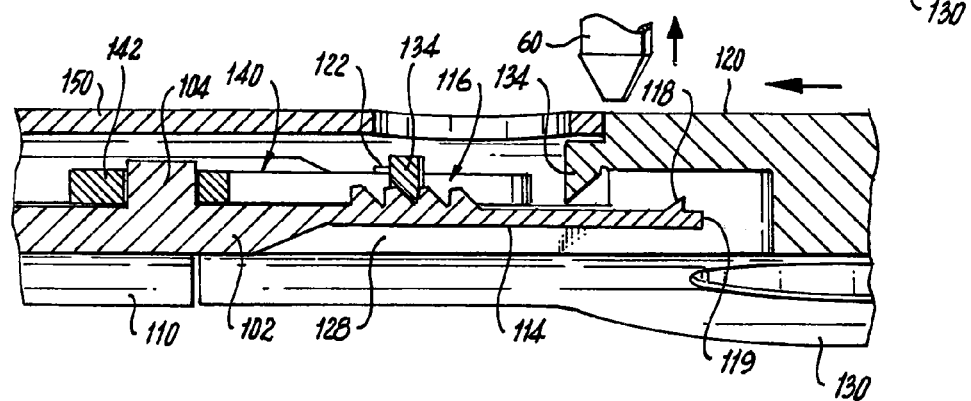
*Fig. 6*
*Fig. 7*

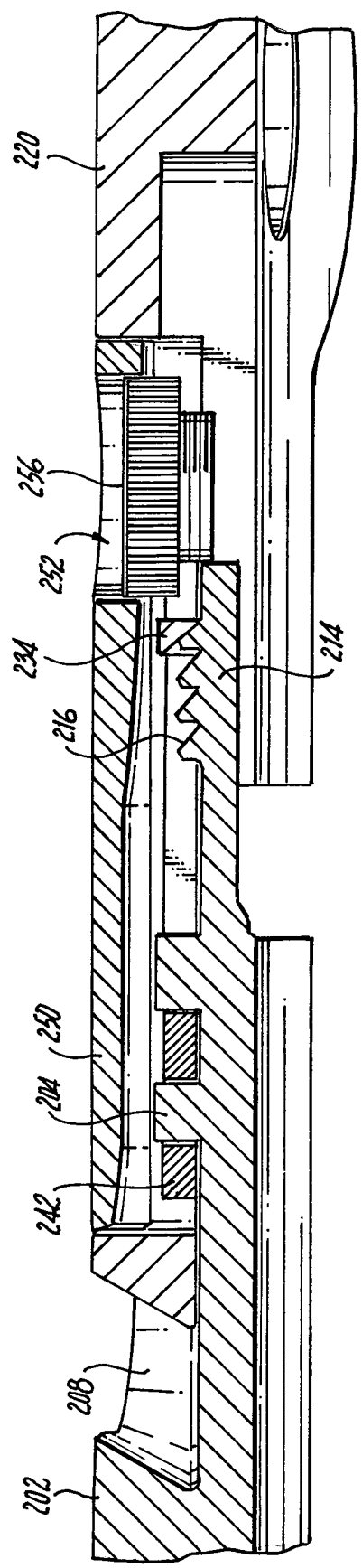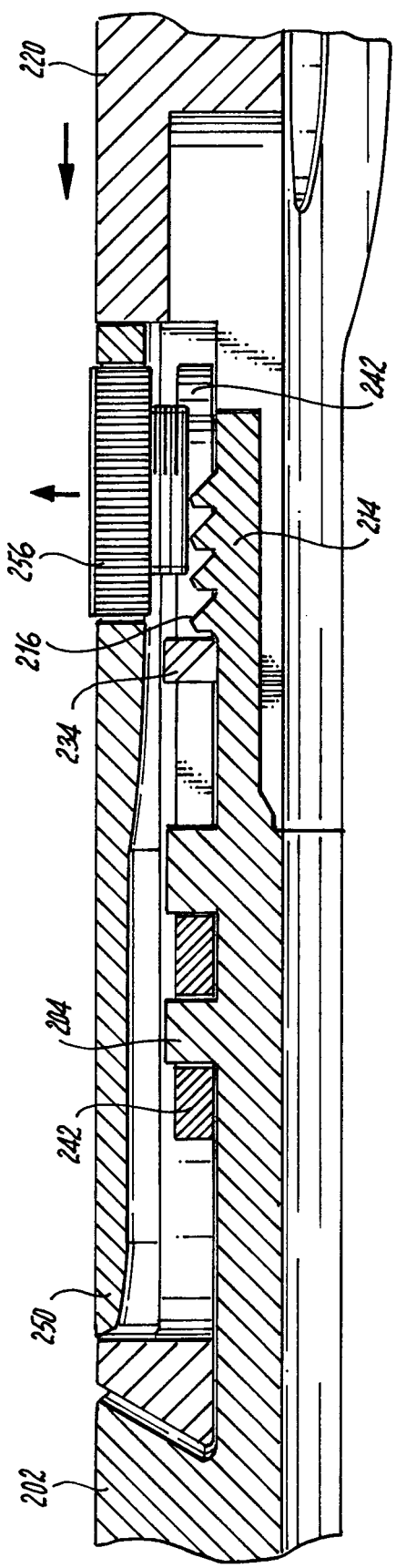
Fig. 11
Fig. 12

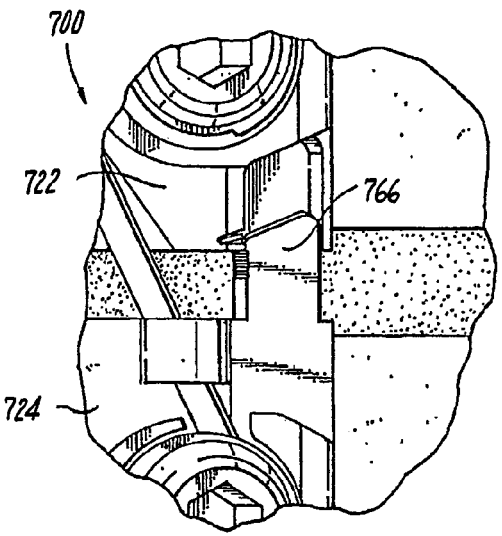
Fig. 18
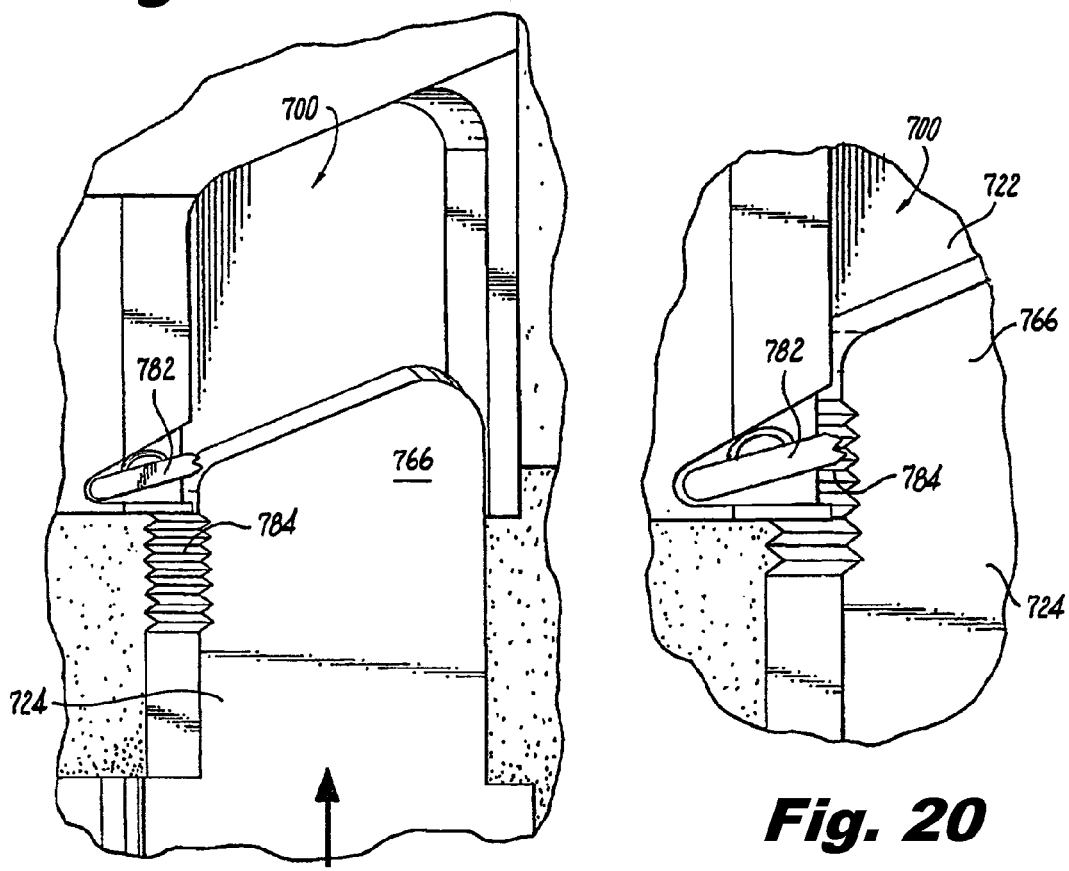
Fig. 19
Fig. 20

DYNAMIC BONE FRACTURE PLATES

CROSS-REFERENCE TO RELATED APPLICATION

This application claims priority to and the benefit of U.S. Provisional Patent Application No. 61/688,247 filed May 10, 2012, U.S. Provisional Patent Application No. 61/704,863 filed Sep. 24, 2012, and U.S. Provisional Patent Application No. 61/803,678 filed Mar. 20, 2013, and is a continuation-in-part of U.S. patent application Ser. No. 13/586,083 filed Aug. 15, 2012, each of which is incorporated herein by reference.

BACKGROUND OF THE INVENTION

1. Field of the Invention

The subject disclosure is directed to surgical implants, and more particularly, to orthopedic bone plates for internally fixating and dynamically stabilizing fractured bones and to screws for use with such bone plates.

2. Description of Related Art

Bone fractures often require stabilization by internal fixation. Bone plates are among the most common orthopedic implants used to stabilize and internally fixate bone fractures. A typical bone plate is a rigid metal plate with guide holes through which bone screws can be passed. Bone screws are usually threaded into the bone above and below the fracture to secure the bone plate, thereby rigidly stabilizing and fixating the fracture.

There has been increasing emphasis on bone plates that are capable of providing compression of the fracture as well as stabilization. Most conventional compression plates however, are made of metal with a modulus of elasticity that is higher than that of bone and therefore, these compression plates have a limited ability to apply controlled amounts of compressive force to a fracture. Moreover, the use of such bone plates produces a mechanical system in which the majority of the stress is borne by the plate rather than the bone. This can impair the healing process in a fractured bone. Furthermore, it is now known that a controlled compressive load should be maintained across a fracture to promote rapid healing. Conventional, static bone plates do not provide or maintain such conditions.

An example of a dynamic vertebral column plate is disclosed in U.S. Patent PG Publication No. 2010/0234895 to Hess published on Sep. 16, 2010, the disclosure of which is herein incorporated by reference in its entirety for purposes of enablement.

SUMMARY OF THE INVENTION

Clearly, there is a need in the art for a dynamic bone plate that can be readily used to stabilize bone fractures.

In one embodiment, the subject technology is directed to a bone fracture plate assembly including a female plate portion and a male plate portion. The female plate portion has an upstanding post, a female dovetail, two apertures for fasteners, and an arm extending from a first end parallel to the female plate portion. The arm has a plurality of ratchet teeth grouped together. The male plate portion has two upstanding posts, a male dovetail for coupling into the female dovetail so that the plate portions only move linearly with respect to each other, a slot for receiving the arm, two apertures for fasteners, and a pawl for engaging the ratchet teeth. A spring dynamically connects the plate portions by applying a compressive load therebetween. The spring has a head portion defining a hole for coupling to the post of the female plate portion as well as a pair of elongated ears extending from the head portion. Each ear defines a slot for coupling to the posts of the male plate portion, respectively. The male dovetail inserts in the female dovetail so that the arm extends into the slot of the male plate portion and the ratchet teeth are engaged by the pawl to retain the plate portions together, and the spring mounts on the posts of the plate portions such that the spring biases the male and female plate portions together.

The arm may also include a first tooth on a distal end, the first tooth being linearly spaced from the plurality of ratchet teeth. The first tooth interacts with a second pawl on the male plate portion for selectively locking the bone fracture plate assembly in an open position in which the male and female plate portions are held apart. The arm is deflectable so that the first tooth can be disengaged from the second pawl to unlock the plate portions.

A top plate couples to the male and female plate portions for covering the spring. The top plate defines a hole for allowing a user to deflect the arm to separate the first tooth from the second pawl so that the spring dynamically biases the male and female plate together. The spring has a generally V-shape. The hole of the spring and the post of the female plate portion are square-shaped to prevent rotation of the spring with respect to the female plate portion.

In another embodiment, the subject technology is directed to a bone plate assembly including at least first and second plate segments adapted and configured for movement relative to one another from a spaced apart position and an approximated position. Ratchet means allowing the first and second plate segments to move from the approximated position while preventing the first and second plate segments from moving toward a spaced apart position. The ratchet means includes a ratcheting pawl member operatively associated with the first plate segment and a rack of ratchet teeth provided on the second plate segment for interacting with the pawl member.

In still another embodiment, the subject technology is directed to a bone fracture plate assembly including a first plate portion, a second plate portion coupled to the first plate portion so that the plates move with respect to each other linearly, and a spring tensioning mechanism for dynamically connecting the first and second plate portions such that when mounted on opposite sides of a bone fracture, the first and second plate portions apply a compressive load to the bone fracture.

Preferably, first means are provided for selectively limiting travel together between the first and second plate portions to create an open position and second means are provided for selectively limiting separation between the first and second plate portions to create a closed position. The first means can be a distal ratchet tooth and a first pawl associated with the first and second plate portions, respectively, and the second means can be a set of ratchet teeth and a second pawl associated with the first and second plate portions, respectively. Adjustment means are associated with at least one of the plate portions for adjusting a force vector of the spring tensioning means relative to an angle of the bone fracture. In one embodiment, the spring tensioning mechanism is a spring mounted on posts and the adjustment means is a plurality of mounting locations for the spring. Also, adjustment means can be associated with at least one of the plate portions for applying a pre-load to the compression mechanism (e.g., spool can be turned, plate can be selectively ratcheted by surgeon, etc.).

It should be appreciated that the present technology can be implemented and utilized in numerous ways, including without limitation as a kit, a process, an apparatus, a system, a device, a method for applications now known and later developed. These and other unique features of the technology disclosed herein will become more readily apparent from the following description and the accompanying drawings.

BRIEF DESCRIPTION OF THE DRAWINGS

So that those having ordinary skill in the art to which the disclosed technology appertains will more readily understand how to make and use the same, reference may be had to the following drawings.

FIG. 5 is a perspective view of the bone plate assembly showing a tool urging the arm to transition from the open to the closed position.

FIG. 6 is a partial sectional local view taken at line 6-6 of FIG. 5 to illustrate transition to the dynamic or closed position.

FIG. 7 is a partial sectional local view taken at line 7-7 of FIG. 5 to illustrate the dynamic closed position.

FIG. 11 is a sectional view of the bone plate assembly of FIG. 10 in the static or open position.

FIG. 12 is a sectional view of the bone plate assembly of FIG. 10 in the dynamic or closed position.

FIG. 18 is a plan view of a section of a plate assembly of the subject invention, illustrating a ratchet mechanism on the outer bars that allows two plate segments to move toward one another to shorten the length of the plate assembly, while preventing the two segments from moving apart from one another.

FIG. 19 is an enlarged localized view of the ratchet mechanism shown in FIG. 18 when the plate segments are spaced apart from one another.

FIG. 20 is a localized view of the ratchet mechanism of FIG. 18 showing the plate segments in an approximated position, in which the ratchet arm prevents the plate segments from moving apart from one another.

FIG. 26A is a cross-sectional view of the bone plate assembly of FIG. 26.

DETAILED DESCRIPTION OF PREFERRED EMBODIMENTS

Figure 1:
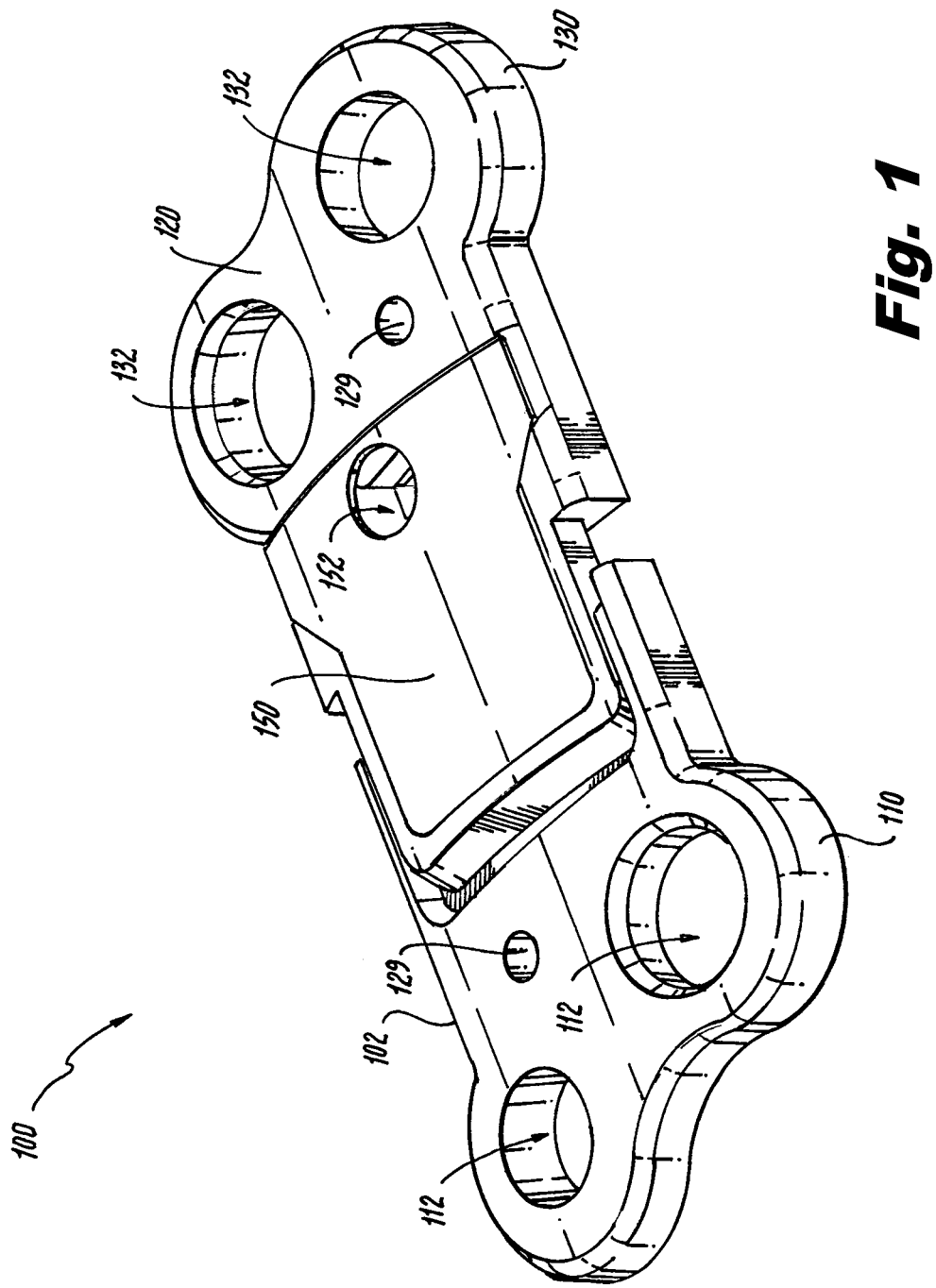
FIG. 1 is a perspective view of a bone plate assembly in the static or open position in accordance with the subject technology.

The present disclosure overcomes many of the prior art problems associated with dynamic bone fracture plates. The advantages, and other features of the technology disclosed herein, will become more readily apparent to those having ordinary skill in the art from the following detailed description of certain preferred embodiments taken in conjunction with the drawings which set forth representative embodiments of the present invention and wherein like reference numerals identify similar structural elements.

All relative descriptions herein such as left, right, up, and down are with reference to the Figures, and not meant in a limiting sense. The illustrated embodiments can be understood as providing exemplary features of varying detail of certain embodiments, and therefore, features, components, modules, segments, mechanisms, elements, and/or aspects of the illustrations can be otherwise combined, interconnected, sequenced, separated, interchanged, positioned, and/or rearranged without materially departing from the disclosed systems or methods. Additionally, the shapes and sizes of components are also exemplary and unless otherwise specified, can be altered without materially affecting or limiting the disclosed technology.

Referring to FIG. 1, a perspective view of a bone fracture plate assembly 100 in a static or open position in accordance with the subject technology is shown. In brief overview, the bone fracture plate assembly 100 provides not only stabilization but compression to facilitate advantageous healing of the bone fracture. In some embodiments, the compression force or vector is parallel to the length of the bone fracture plate assembly 100. The compression force may also be at an angle with respect to the length and even variable to match a particular application as described below with respect to different embodiments.

The bone fracture plate assembly 100 includes a female plate portion 102 coupled to a male plate portion 120. The plate segments or plate portions 102, 120 are adapted and configured for movement relative to one another from a spaced apart or "open" position and an approximated or "closed" position. Various means allow the plate portions 102, 120 to move from open to closed while preventing the plate portions 102, 120 from moving toward a spaced apart position. Further, the open position is static, in which the bone fracture plate assembly 100 does not apply compression whereas the closed position is dynamic, in which the bone fracture plate assembly 100 applies compression.

Figure 2:
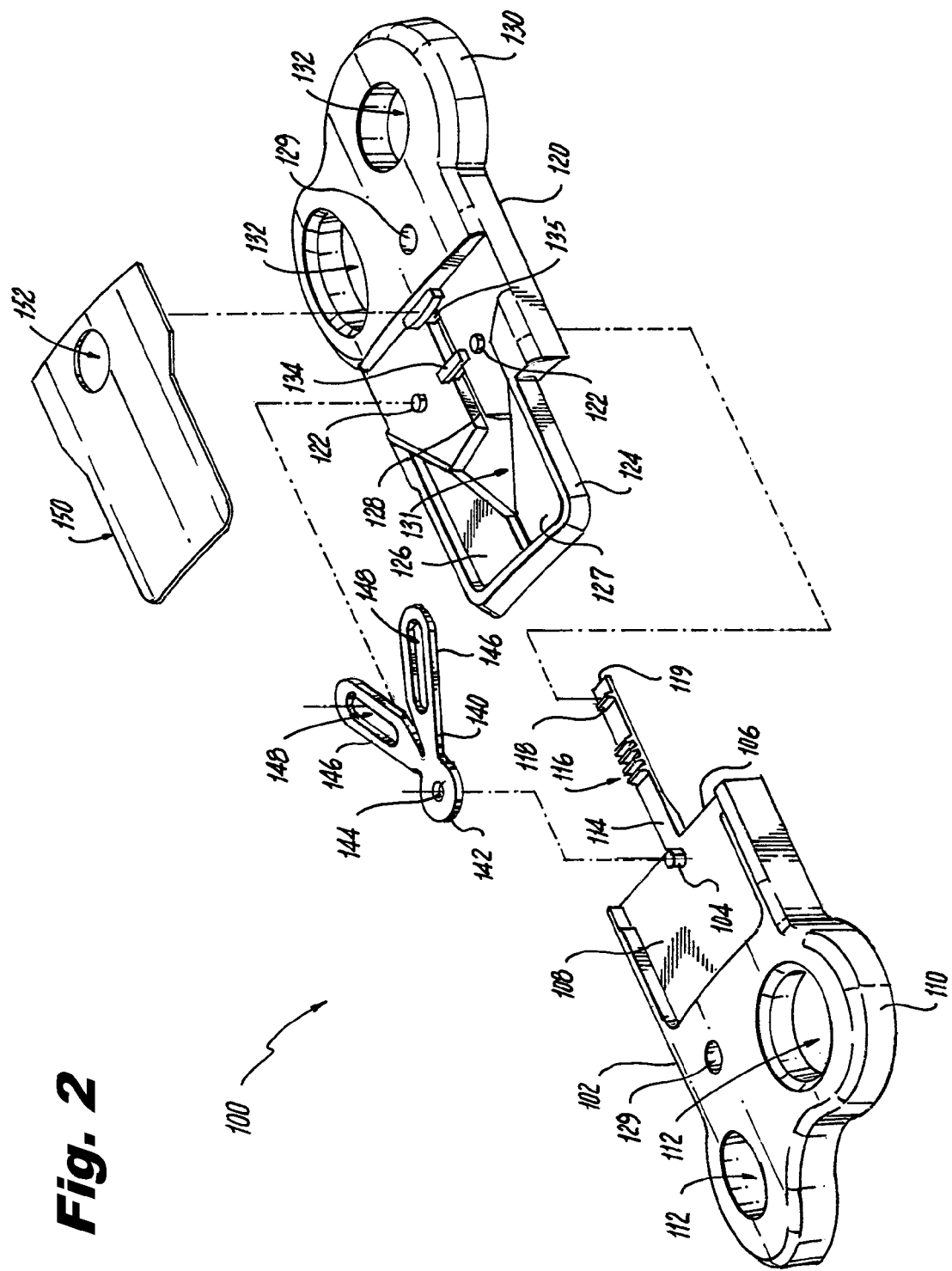
FIG. 2 is an exploded perspective view of the bone plate assembly of FIG. 1.

Referring now to FIG. 2, an exploded perspective view of the bone fracture plate assembly of FIG. 1 is shown. The female plate portion 102 has an upstanding post 104 located near a first end 106. The female plate portion 102 defines a female dovetail 108. A second end 110 of the female plate portion 102 defines two apertures 112 for fasteners (not shown) that attached the female plate portion 102 to bone.

An arm 114 extends from the first end 106 parallel to the female plate portion 102. The arm 114 has a plurality of ratchet teeth 116 grouped in an intermediate location. The arm 114 also includes a tooth 118 on a distal end 119, the tooth 118 being linearly spaced from the grouped teeth 116.

The male plate portion 120 has two upstanding posts 122. A first end 124 of the male plate portion 120 defines a male dovetail 126 that couples into the female dovetail 108 so that the plate portions 102, 120 only move linearly with respect to each other when the dovetails 108, 126 are engaged. The dovetail shapes may be rounded, L-shaped, angular and other configurations to allow substantially only linear movement when coupled. A second end 130 of the male plate portion 120 defines two apertures 132, similar to the female plate portion 102, for bone fasteners (not shown). Each plate portion 102, 120 defines a tack hole 129.

The male plate portion 120 defines a slot 128 for receiving the arm 114, wherein the slot 128 terminates in an open area 131 that is lower than the adjacent area 127. In one embodiment, the open area 131 is about 0.6 mm lower that the adjacent area 127. The male plate portion 120 has a first pawl 134 for engaging the ratchet teeth 116 in the closed position (see FIG. 7) and a second pawl 135 for engaging the distal tooth 118 in the open position (see FIG. 4). The pawls 134, 135 may extend into the slot 128 or the teeth 116, 118 may extend upward out of the slot 128, or both to accomplish the interaction.

Figure 4:
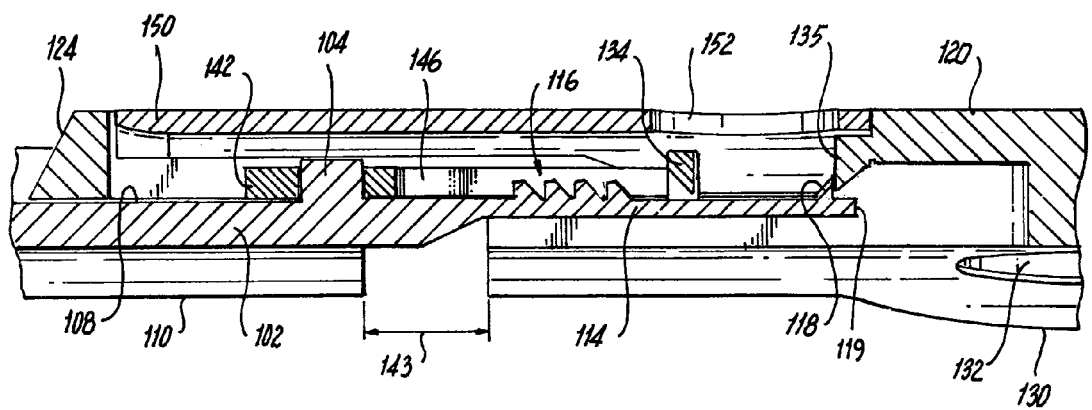
FIG. 4 is a partial sectional local view taken at line 4-4 of FIG. 3 to illustrate the locking of the bone fracture plate assembly in the static or open position.

As best seen in FIG. 4, in the open position, only the distal tooth 118 and second pawl 135 are engaged. This engagement prevents the bone fracture plate assembly 100 from moving to the closed position. In other words, the distal tooth 118 and second pawl 135 are configured to hold the plate portions 102, 120 slightly separated, hence in the open position. The amount of separation or gap 143 between the plates 102, 120 is preferably about 2 mm. In other embodiments, the gap 143 is less or more than 2 mm with a range of 2-5 mm being appropriate for most applications. As best seen in FIG. 6, in order to release the engagement of the distal tooth 118 and second pawl 135, the arm 114 is deflectable so that the distal tooth 118 can be disengaged from the second pawl 135. When released, the plate portions 102, 120 are pulled into the closed position by a spring 140.

Figure 3:
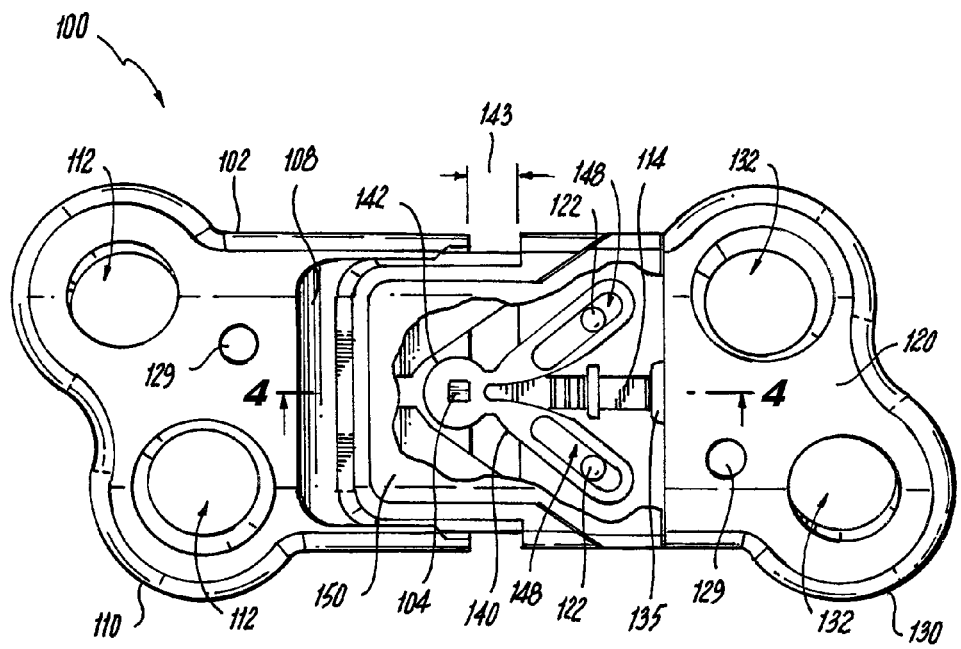
FIG. 3 is a top view of the bone plate assembly of FIG. 1 with a portion of the top plate cutaway.

Referring to FIGS. 2 and 3 and 5, the spring 140 extends from the female plate portion post 104 to the male plate portions posts 122 to dynamically connect the plate portions 102, 120 by applying a compressive load therebetween. The spring 140 has an apex or head portion 142 defining a hole 144 for coupling to the post 104. Preferably, the hole 144 of the spring 140 and the post 104 of the female plate portion 102 are square-shaped to prevent rotational movement of the spring 140. Triangular, star, rectangular, trapezoidal, hexagon, keyhole and many shapes as well as simply spot welding, clipping, pinning, and screwing the spring 140 to the female plate portion 102 would accomplish the same result of rotationally fixing the spring 140 with respect to the female plate portion 102. The post 104 and hole 144 may also be round to allow for rotation.

A pair of elongated ears 146 extend from the head portion 142. Each ear 146 defines a slot 148 for coupling to the posts 122 of the male plate portion 120, respectively. The posts 122 are shaped so that the posts 122 can freely move within the slots 148. The generally V-shape of the spring 140 creates a compression force between the plates 102, 120 that generally biases the plates 102, 120 together. As noted above, in the open position, the engagement of the distal tooth 118 and second pawl 135 prevents the spring's compression force from bringing the plates 102, 120 together.

In a preferred embodiment, the spring 140 is fabricated from a memory alloy such as nitinol so that the ears will press outward on the posts 122 to create a force vector that pulls the plates 102, 120 together. The spring may take many different shapes as well such as a C-shape, a U-shape, a M-shape with two flex points, a V-shape as well as more typical coil and flexure spring arrangements, whether it be one or a plurality of springs to create the desired force.

Referring to FIGS. 1-7, the bone fracture plate assembly 100 also includes a top plate 150 coupled to the plate portions 102, 120 for covering the spring 140. The top plate 150 is preferably welded to one of the plate portions 102, 120. In another embodiment, the top plate includes a lip that is captured in the dovetails 108, 126 when assembled. The top plate may also include a depending projection (not shown) that engages the female plate portion 102 and the spring 140 to fix the head portion 142 to the female plate portion 102. The top plate 150 defines a hole 152 for allowing the surgeon to deflect the aim 118 as described below with respect to FIGS. 6, 7 and 9.

Referring now to FIG. 4, as noted above, when assembled, the male dovetail 126 inserts in the female dovetail 108 so that the arm 114 extends into the slot 128 and the spring 140 is placed over the posts 104, 122. Although the spring 140 urges the plate portions 102, 120 together, the distal tooth 118 engages the second pawl 135 to maintain the bone fracture plate assembly 100 open. The top cover 150 is in place and the bone fracture plate assembly 100 is ready for deployment.

Figure 8:
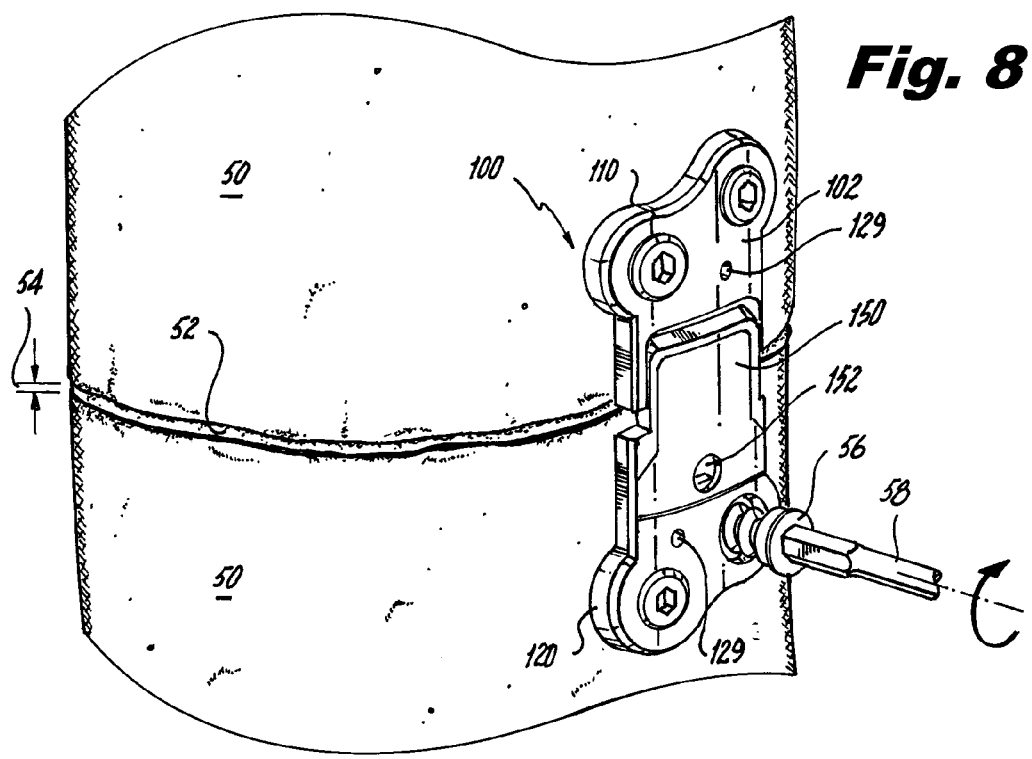
FIG. 8 is a perspective view of a bone plate assembly being fastened to a bone in the static or open position in accordance with the subject technology.

Referring now to FIG. 8, a perspective view of the bone fracture plate assembly 100 being fastened to a bone 50 with a fracture 52 is shown. Preferably, the fracture 52 has a gap 54 that will be closed by the bone fracture plate assembly 100. Initially, the bone fracture plate assembly 100 is in the static or open position. The surgeon places the bone fracture plate assembly 100 on the bone 50 so that the length of the bone fracture plate assembly 100 is perpendicular to the bone fracture 52. This aligns the compression force vector to be perpendicular to the bone fracture 52 as well.

To hold the bone fracture plate assembly 100 in place, the surgeon may use a temporary fastener (not shown) in the tack holes 129 to temporarily mount the bone fracture plate assembly 100. The tack holes 129 are particularly useful when the bone fracture plate assembly 100 is not preassembled and/or does not include a locking mechanism to maintain the open condition. In such case, the surgeon partially assembles the bone fracture plate assembly in place, may tack it down and engage the spring mechanism. The tack holes 129 can also be used after screw insertion with a tool to "pre-compress" the plate by pinching the plate segments together.

Still referring to FIG. 8, after tacking the bone fracture plate assembly 100 temporarily in place in the open position, the surgeon fixes the bone fracture plate assembly 100 more permanently by inserting bone fasteners 56 through the holes 112, 132 and into the bone 50 with a screwdriver 58.

Figure 9:
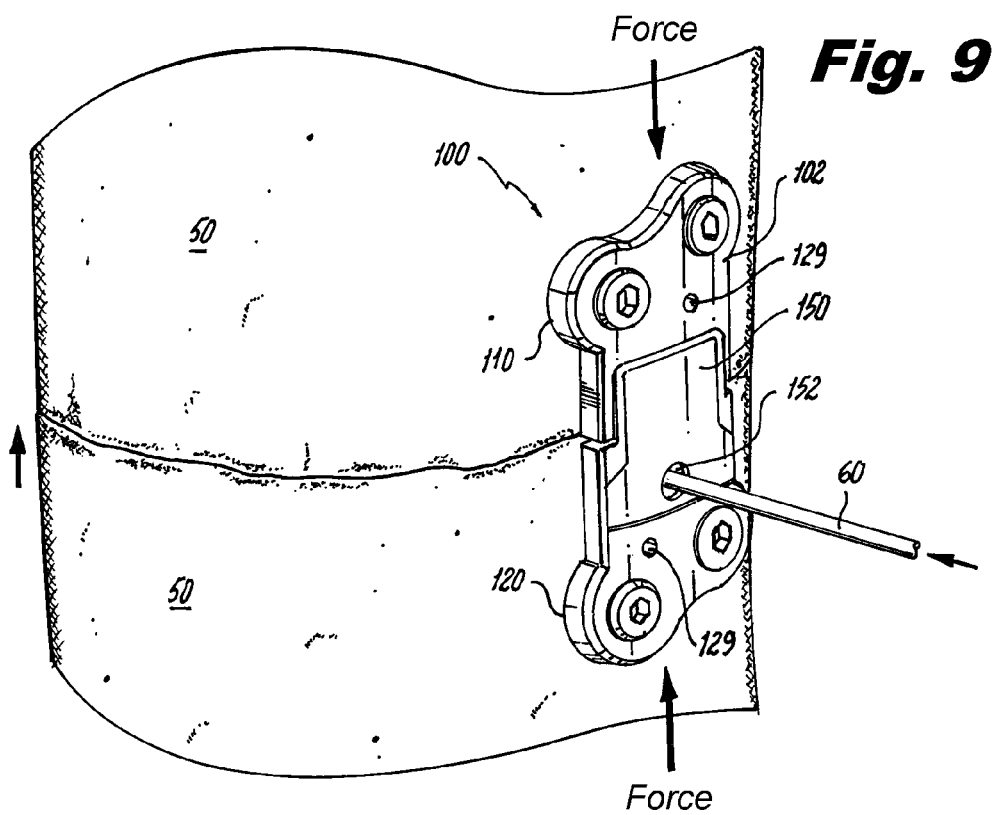
FIG. 9 is a perspective view of a bone plate assembly fastened to a bone in the dynamic or closed position in accordance with the subject technology.

Referring to FIGS. 6 and 9, after fixing the bone fracture plate assembly 100 about the fracture, the surgeon uses a pointed tool 60 to momentarily deflect the arm 114 so that the distal tooth 118 disengages the second pawl 135. At this point, the compression force of the spring 140 pulls the plate portions 102, 120 together to close not only the plate gap 143 but the bone fracture 52/bone fracture gap 54 as well. It is envisioned that the plate portions 102, 120 do not need to completely close.

Referring now to FIG. 7, a sectional local view taken at line 7-7 of FIG. 5 illustrates the dynamic closed position. As the plate portions 102, 120 come together into the closed position, the distal tooth 118 moves away from the second pawl 135 so that when the arm 114 returns to the normal position, the distal tooth 118 no longer engages the second pawl 135. In another embodiment, the arm 118 bends permanently out of the way. For example, the arm 118 may have a crease, indentation or other predefined weak area upon which the arm 118 bends so that once pushed out of the way, the distal tooth 118 and the second pawl 135 do not re-engage.

As the plate portions 102, 120 come together, the first pawl 134 and the plurality of teeth 116 become engaged to prevent the plate portions 102, 120 from subsequently moving apart. Even though the bone fracture has been closed by the bone fracture plate assembly 100, the spring 140 continues to apply a compressive force across the fracture to aid in the healing process.

Figure 10:
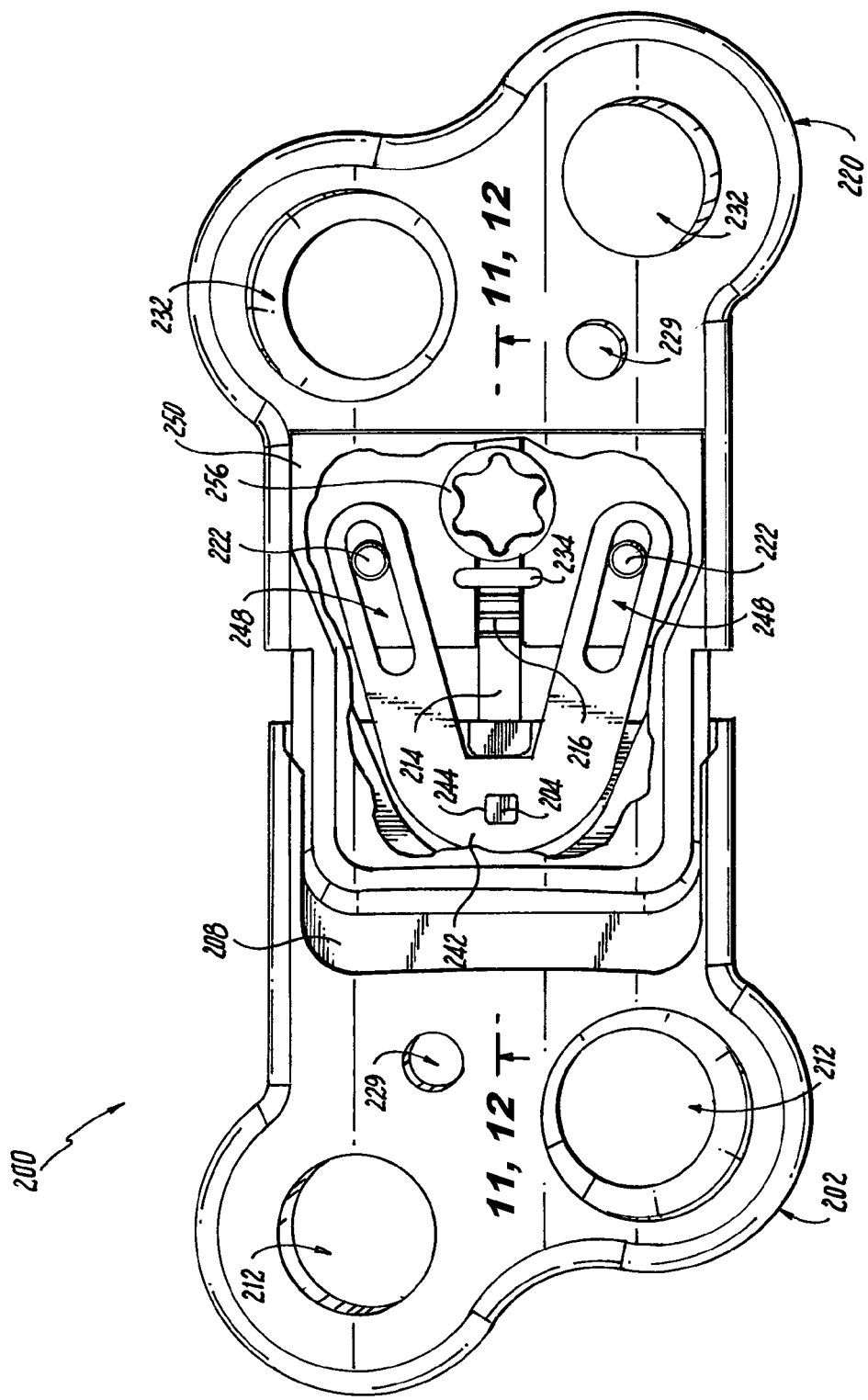
FIG. 10 is a top view of another bone plate assembly in the static or open position in accordance with the subject technology.

Referring now to FIGS. 10-12, a top open, an open sectional and a closed sectional view, respectively, of another bone fracture plate assembly 200 in accordance with the subject technology is shown. As will be appreciated by those of ordinary skill in the pertinent art, the bone fracture plate assembly 200 utilizes similar principles to the bone fracture plate assembly 100 described above. Accordingly, like reference numerals preceded by the numeral "2" instead of the numeral "1", are used to indicate like elements. The primary difference of the bone fracture plate assembly 200 in comparison to the bone fracture plate assembly 100 is the modification of the structure to maintain the bone fracture plate assembly 200 in the open position. Thus, the following description mainly addresses this modification.

In the open position shown in FIG. 11, the male plate portion 220 still defines a slot 228 into which the arm 214 extends but a captive screw 256 extends into the slot 228 to act as a stop against the distal end 219 of the arm 214. Once the bone fracture plate assembly 200 is fixed in place about a fracture, the surgeon backs out the captive screw 256 (or removes the screw 256 altogether depending upon how it is configured), to allow the plate segments 202, 220 to come together in the dynamic or closed position.

Figure 13:
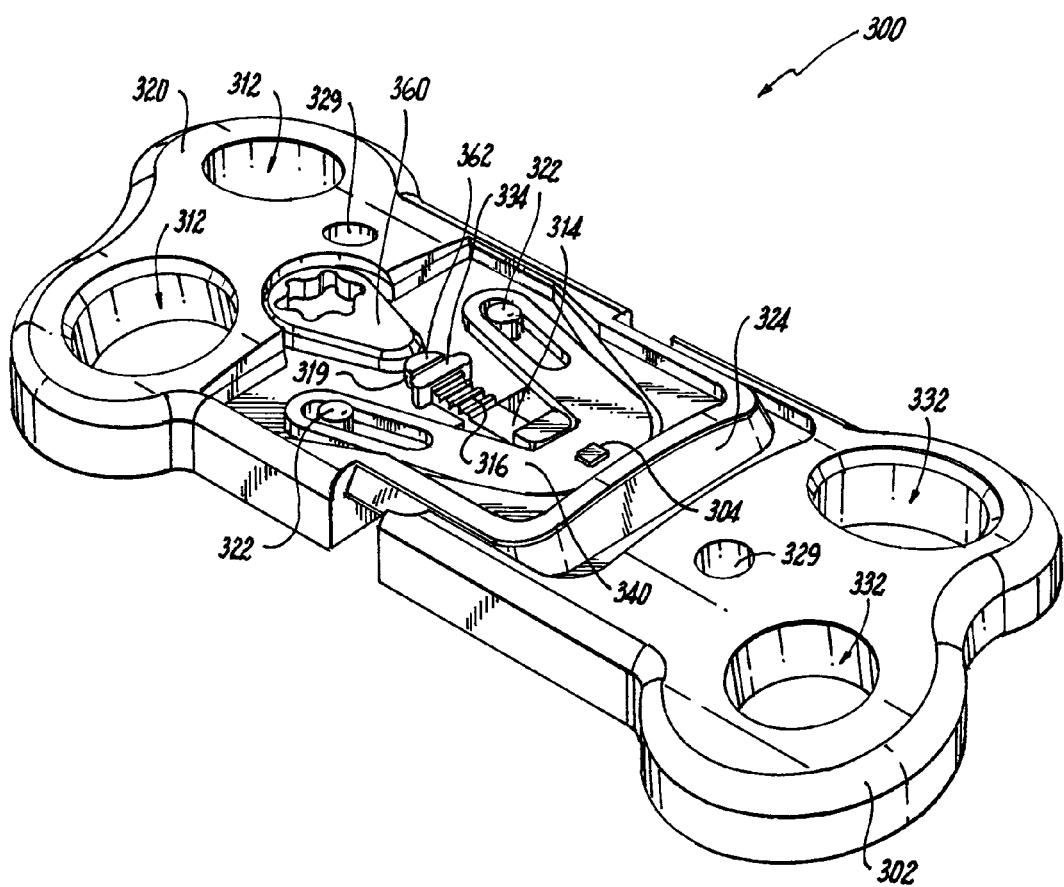
FIG. 13 is a perspective view of still another bone plate assembly in the static or open position in accordance with the subject technology.
Figure 14:
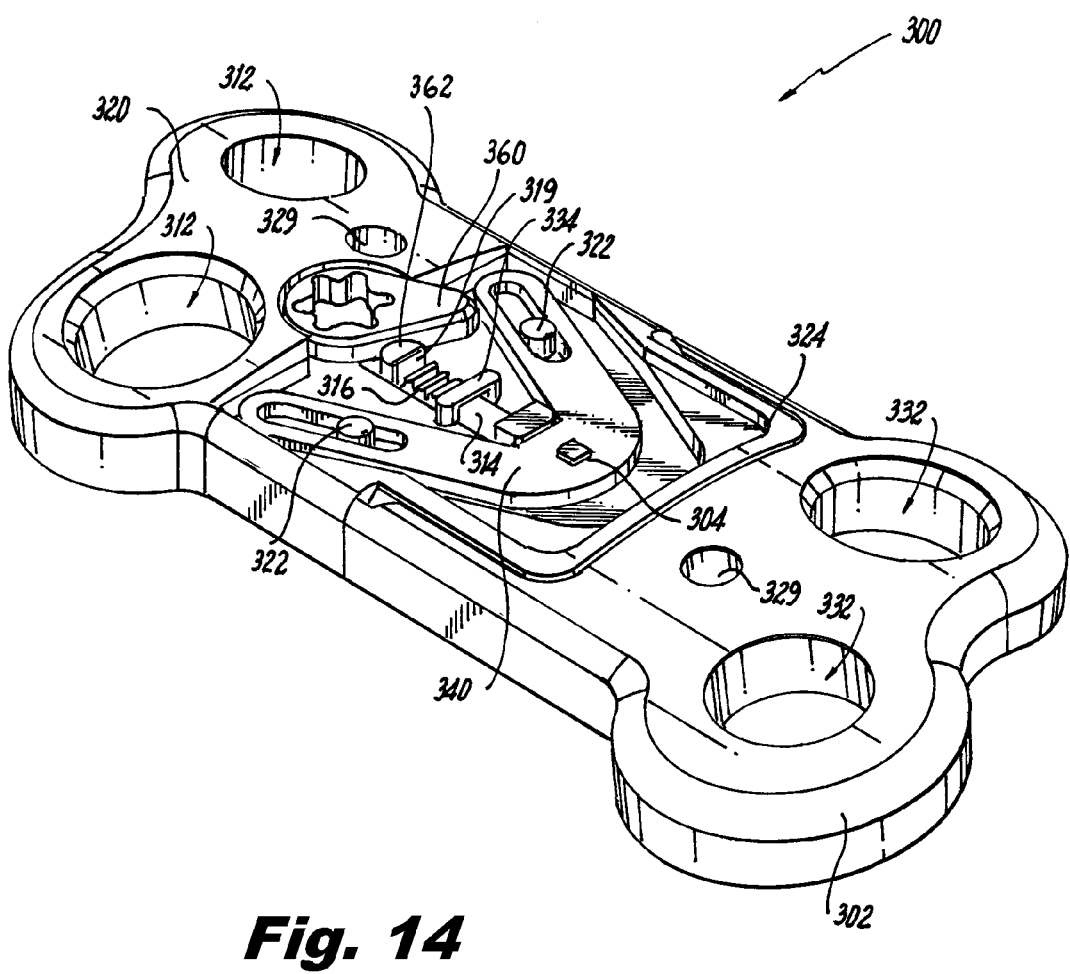
FIG. 14 is a perspective view of the bone plate assembly of FIG. 13 in the closed position.

Referring now to FIGS. 13 and 14, a perspective open and a perspective closed view, respectively, of another bone fracture plate assembly 300 in accordance with the subject technology is shown. As will be appreciated by those of ordinary skill in the pertinent art, the bone fracture plate assembly 300 utilizes similar principles to the bone fracture plate assemblies 100, 200 described above. Accordingly, like reference numerals preceded by the numeral "3" instead of the numeral "1" or "2", are used to indicate like elements. The primary difference of the bone fracture plate assembly 300 is again modification of the structure to maintain the bone fracture plate assembly 300 in the open position. Thus, the following description mainly addresses this modification.

In the open position shown in FIG. 13, the male plate portion 320 includes a selectively rotatable cam 360 that engages a block 362 on the distal end 319 of the arm 314. The block 362 may define a cupped surface (not explicitly referenced), that helps capture the cam 360. The cam 360 and block 362 are sized so that when engaged, the bone fracture plate assembly 300 remains open against the spring force. To transition to the dynamic closed position in FIG. 14, the surgeon simply rotates the cam 360 off the block 362. The cam 360 can be rotated back to re-engage the block 362 to spread the plate segments 302, 320 back to the open position.

Figure 15:
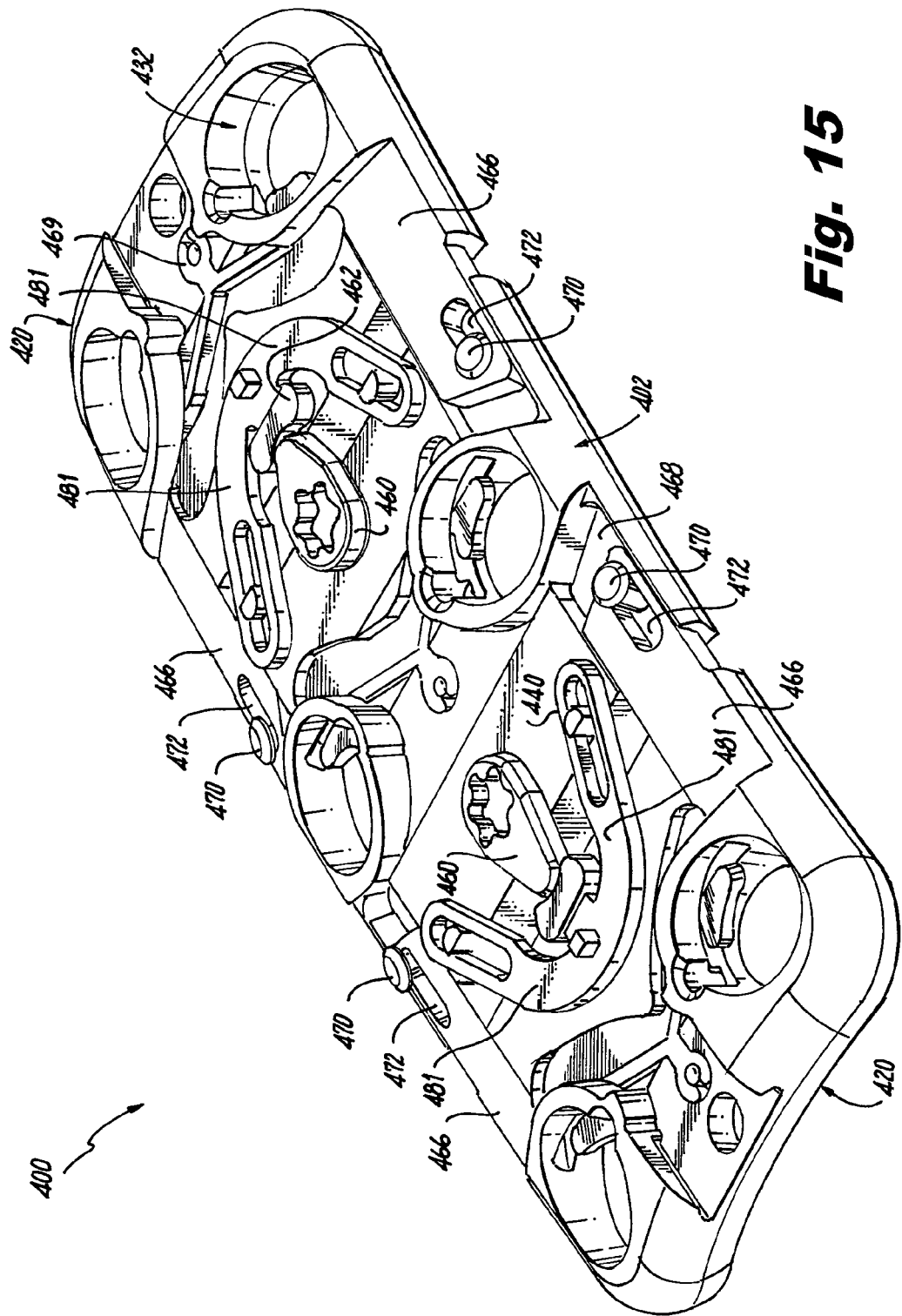
FIG. 15 is a perspective view of yet another bone plate assembly in the static or open position in accordance with the subject technology.

Referring now to FIG. 15, a perspective view of yet another bone fracture plate assembly 400 in the static or open position in accordance with the subject technology is shown. Again, the bone fracture plate assembly 400 utilizes similar principles to the previously discussed bone fracture plate assemblies 100, 200, 300 so similar numbering is used. The bone fracture plate assembly 400 includes a central female plate segment 402 and two outer male plate segments 420.

To lock the bone fracture plate assembly 400 in the open position, cams 460 are set against cupped blocks 462. To unlock the bone fracture plate assembly 400, the cams 460 are rotated away from the blocks 462. Rather than central dovetails, the bone fracture plate assembly 400 has at least one bar 466 extending from the male plate segments 420 into a groove 468 formed in the female plate segment 402. In the preferred embodiment, each male plate segment 420 has an outer bar 466 on each side of the spring 440 within a corresponding groove 468 in a sliding arrangement to act as a linear guide. Each bar 466 is coupled to the female plate segment 402 by a pin 470 extending into the female plate segment 402 through a slot 472 formed in the bar 466. Alternatively, the bars 466 and groove 468 may be a dovetail arrangement. The bone fracture plate assembly 400 also includes a fastener locking member 469 that partially extends into the mounting holes to engage a ridge in the fasteners (not shown) or completely cover the fasteners to retain the fasteners. Alternatively, the locking member 469 may seat on top of a shoulder on the fastener to retain the fastener.

Figure 16:
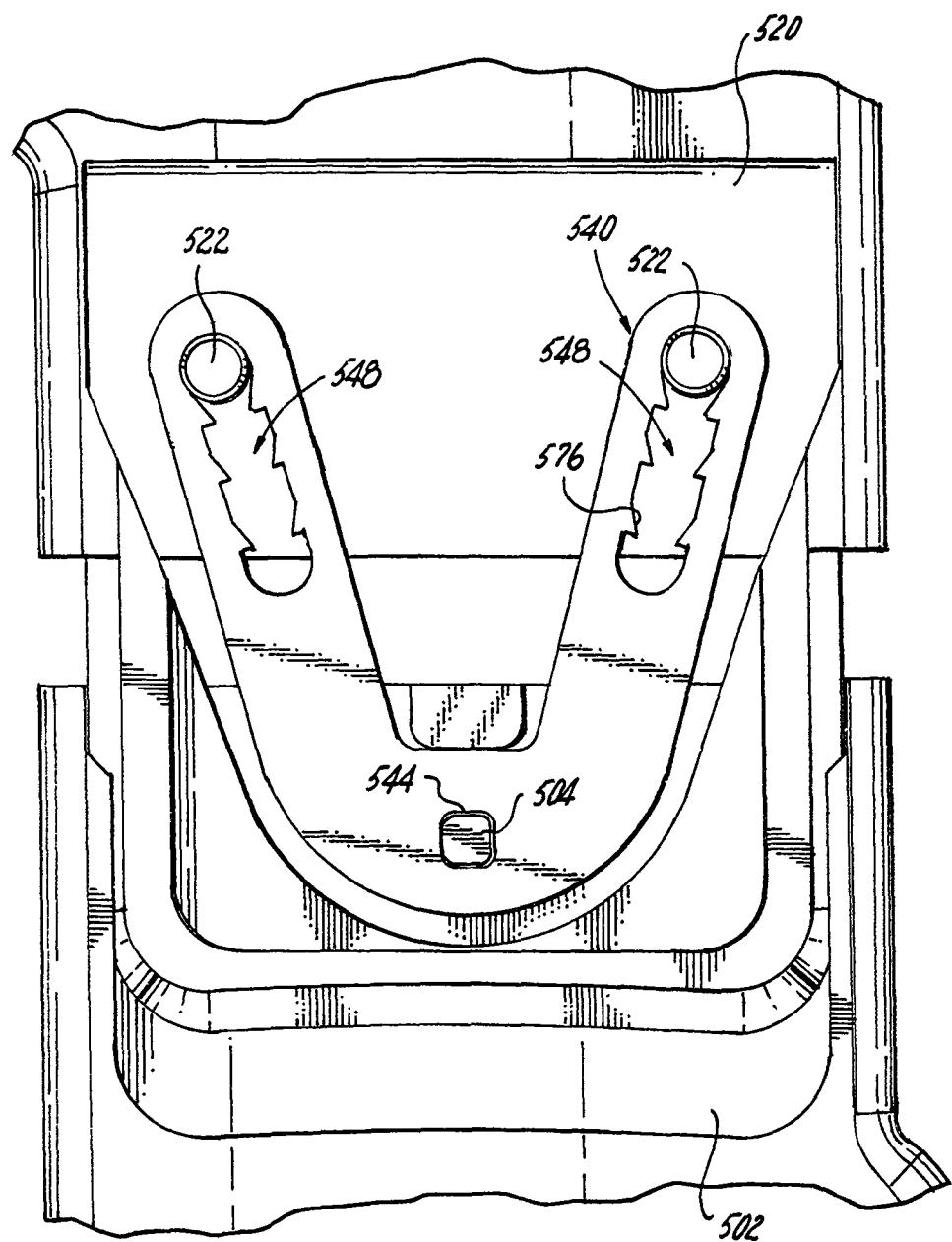
FIG. 16 is a top view of an alternative spring mechanism with a locking feature in accordance with the subject technology.

It is noted that the bone fracture plate assembly 400 does not include ratchet means for allowing the plate segments 402, 420 to move closer together while preventing the plate segments 402, 420 from moving toward a spaced apart position. Referring now to FIG. 16, a top view of an alternative spring 540 with a locking feature 576 that can be utilized with all of subject technology is shown. The spring 540 is V-shaped with an apex hole 544 coupled to a post 504. The slots 548 similarly couple to posts 522 however the slots 548 form a triangular locking feature 576 such that upon the posts 522 moving down the slot 548, the locking feature 576 prevents the posts 522 from moving upward to, in effect, prevent the plates 502, 520 from separating once brought together. The posts 522 may also have a triangular shape to more effectively interact with the triangular locking feature 576. In another embodiment, the slots 548 are arcuate or kidney shaped so that once the posts 522 move from the outer end and overcome the intermediate hump, the posts 522 come to rest in the inner end and are effectively retained there. In another embodiment, the locking feature 576 is simply semi-circular ridges that the posts 522 can pass over but effectively rest in as a plurality of detent positions.

Figure 17:
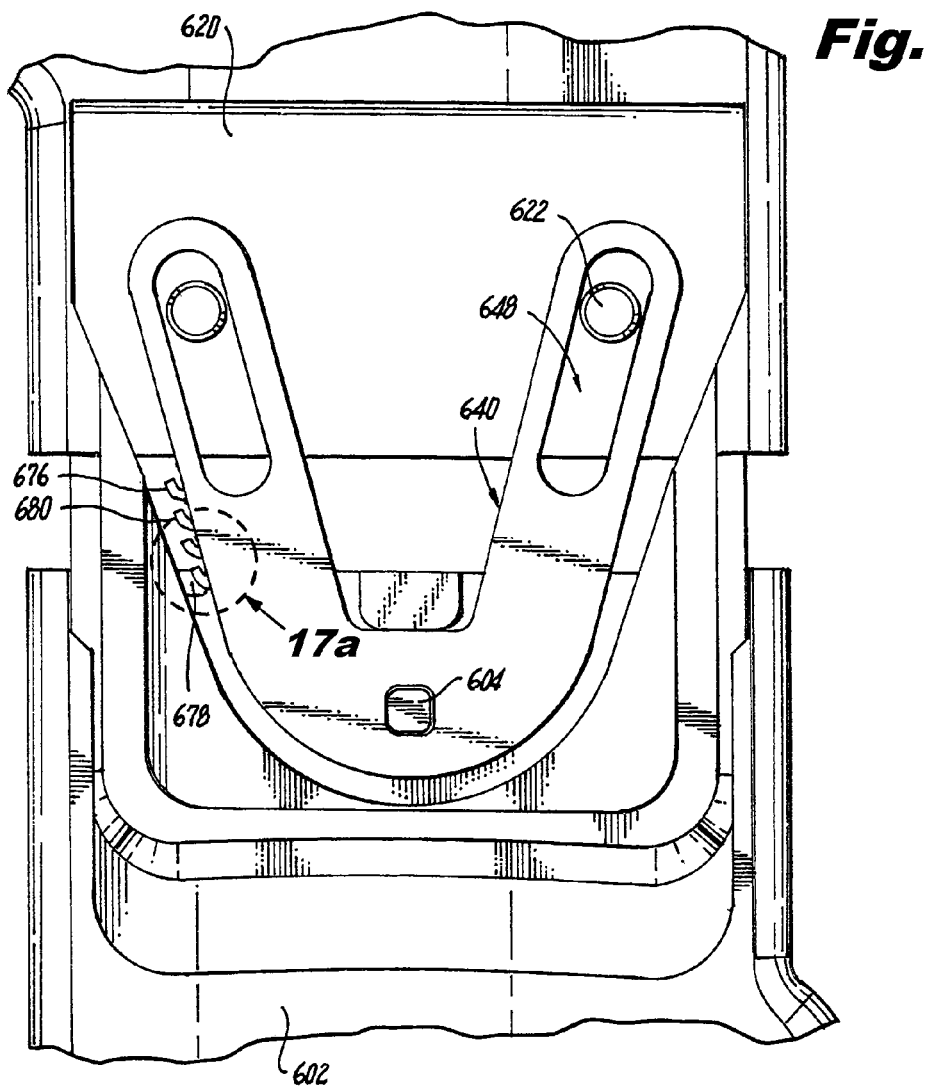
FIG. 17 is a top view of another alternative spring mechanism with a locking feature in accordance with the subject technology.
Figure 17A:
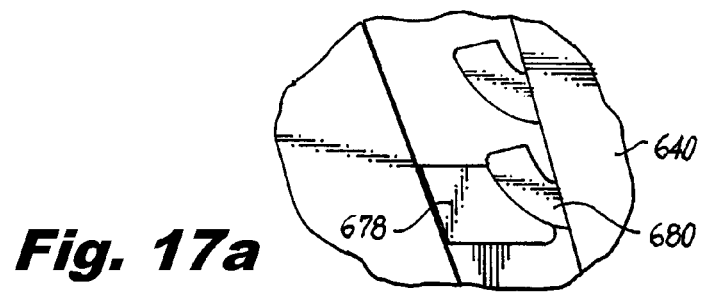
FIG. 17a is a detailed view of the alternative spring mechanism of FIG. 17.

Referring now to FIG. 17 and FIG. 17a, a top view of another alternative spring 640 with a locking feature 676 is shown. The locking feature 676 includes a ratcheting pawl member 678 on the female plate segment 602 and a rack 680 of ratchet teeth provided on the male plate segment 620 for interacting with the pawl member 678.

Referring now to FIG. 18, there is illustrated another dynamic bone plate assembly 700 that includes at least first and second plate segments 722 and 724, which are adapted and configured for movement relative to one another from a spaced apart position shown in FIG. 19 to an approximated position shown in FIG. 20. A ratcheting pawl member 782 is on the first plate segment 722 and a rack of ratchet teeth 784 are provided on the outer bar 766 of the second plate segment 724 for interacting with the pawl member 782. This ratchet mechanism allows the first and second plate segments 722, 724 to move from the spaced apart position of FIG. 19 to the approximated position of FIG. 20, while preventing the first and second plate segments 722, 724 from moving back toward a spaced apart position.

Figure 21:
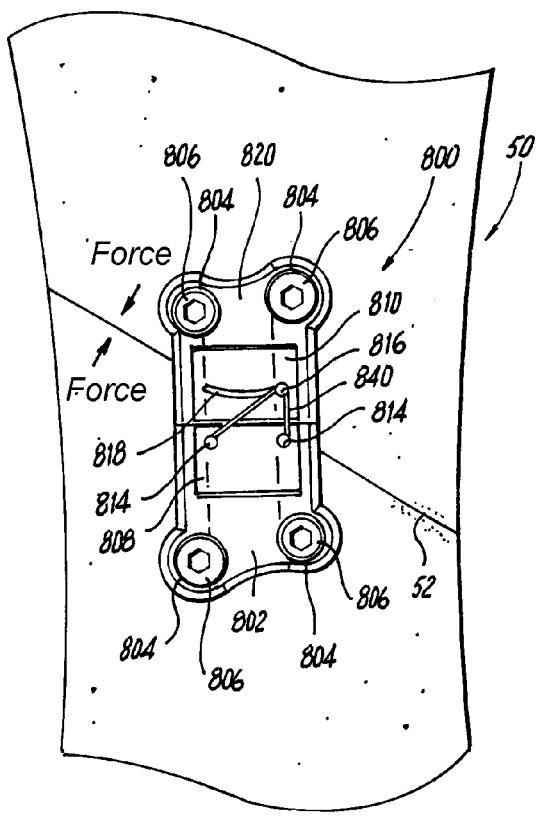
FIG. 21 is a perspective view of a bone plate assembly fastened to a bone in the dynamic or closed position in accordance with the subject technology.

Referring now to FIG. 21, is a somewhat schematic perspective view of a bone fracture plate assembly 800 fastened to a bone 50 in the dynamic or closed position in accordance with the subject technology. The bone fracture plate assembly 800 provides an ability to vary the position of the compressive force vector with respect to the length of the bone fracture plate assembly 800. As a result, for an angled bone fracture 52, the compressive force vector can be aligned to be substantially perpendicular to the angled bone fracture 52.

The bone fracture plate assembly 800 has two opposing plate segments 802, 820 each plate segment 802 defining holes 804 for fasteners 806 for mounting to the bone 50. A first central plate 808 is mounted on one of the plate segments 802 such as by a rivet (not shown). A second central plate 810 is mounted on the other of the plate segments 802. The first central plate 808 has preferably fixed two upstanding posts 814. The second central plate 810 has one upstanding post 816 that movably mounts within an arcuate slot 818. Thus, when the spring 840 is mounted on the posts 814, 816, the post 816 can be moved and locked within the arcuate slot 818 to rotate the compressive force vector to align substantially perpendicularly to the bone fracture 52. The spring 840 may be any of the versions disclosed herein, an elastic, a coiled wire and the like.

Figure 21A:
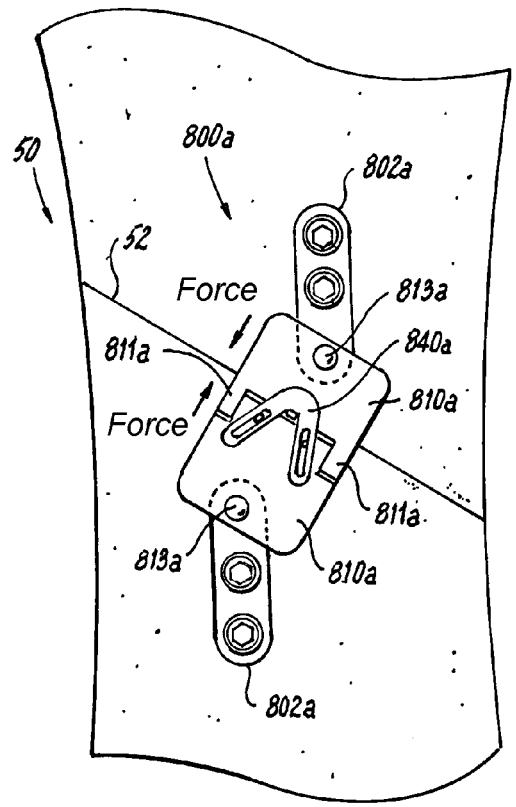
FIG. 21a is a perspective view of another bone plate assembly fastened to a bone in the dynamic or closed position in accordance with the subject technology.

FIG. 21a is a perspective view of another bone plate assembly 800a fastened to a bone 50 in the dynamic or closed position in accordance with the subject technology. The bone plate assembly 800a has outer plates 802a that mount to the bone 50. Each outer plate 802a has a central plate 810a that rotatably extends to cooperate with the opposing central plate 810a via a spring 840a. Linear guides 811a are provided on each side of the spring 840a so that the force vector align with the length of the central plates 810a. Once the bone plate assembly 800a is in place, the pivot point 813a of the central plates 810a can be locked down. For example, the pivot point 813a may be a partially inserted screw, which is fully inserted to lock down the central plates 810a.

Figure 22:
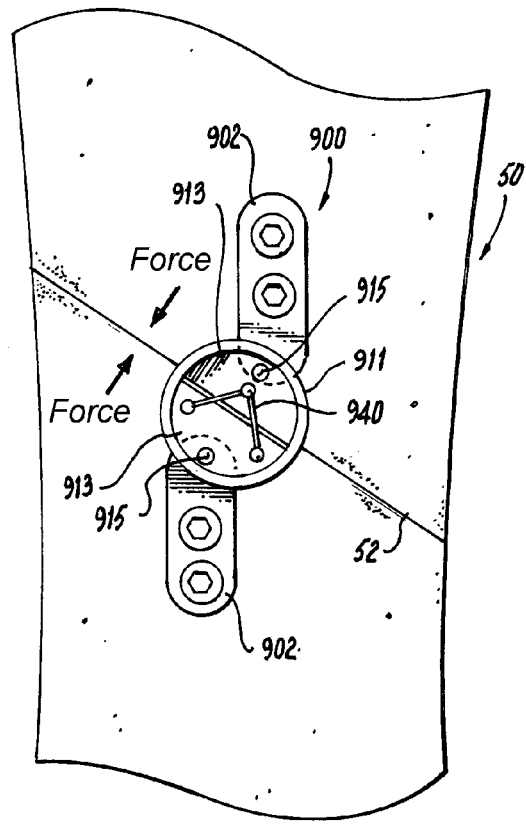
FIG. 22 is a perspective view of a bone plate assembly fastened to a bone in the dynamic or closed position in accordance with the subject technology.

FIG. 22 is a perspective view of another bone plate assembly 900 fastened to a bone 50 in the dynamic or closed position in accordance with the subject technology. The bone plate assembly 900 includes outer plates 902, which may or may not be linearly aligned lengthwise. Instead of opposing central plates 810a like in FIG. 21a, the bone plate assembly 900 has a central disc 911 that can be selectively rotated. The disc 911 has two-sub parts 913 that are separated to allow linear movement therebetween. A spring 940 spans the parts 913 to create a compressive force. Once the bone plate assembly 900 is in place, the pivot point 915 of the disc 911 can be locked down. As noted herein, the disc 911 can be adapted to any of the bone plate assemblies of the subject technology to provide adjustments of the compression force vector to be about perpendicular to the bone fracture.

Figure 23:
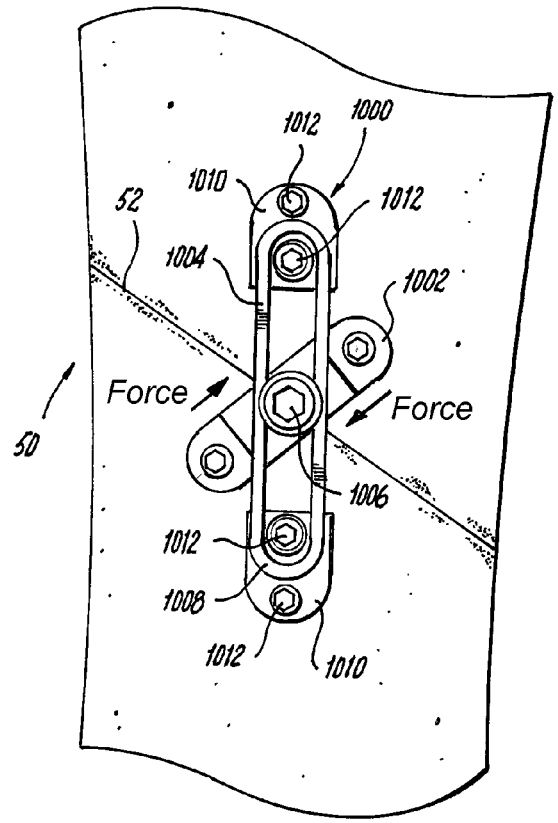
FIG. 23 is a perspective view of a modular plate system fastened to a bone in accordance with the subject technology.

FIG. 23 is a modular plate system 1000 in perspective view. The modular plate system 1000 again allows aligning the compression force vector of one or more bone fracture plate assemblies 1002 perpendicularly to one or more bone fractures 52. The modular plate system 1000 includes a frame 1004 that couples to one or more bone fracture plate assemblies 1002 by one or more bolts 1006.

In FIG. 23, one bone fracture plate assembly 1002 is shown and the ends 1008 of the frame 1004 are coupled to the bone 50 by simple plates 1010 and fasteners 1012. Alternatively, additional and intermediate bone fracture plate assemblies may couple to the frame 1004 so that the frame 1004 provides structural support to the bone 50 or spine as the case may be.

Figure 24:
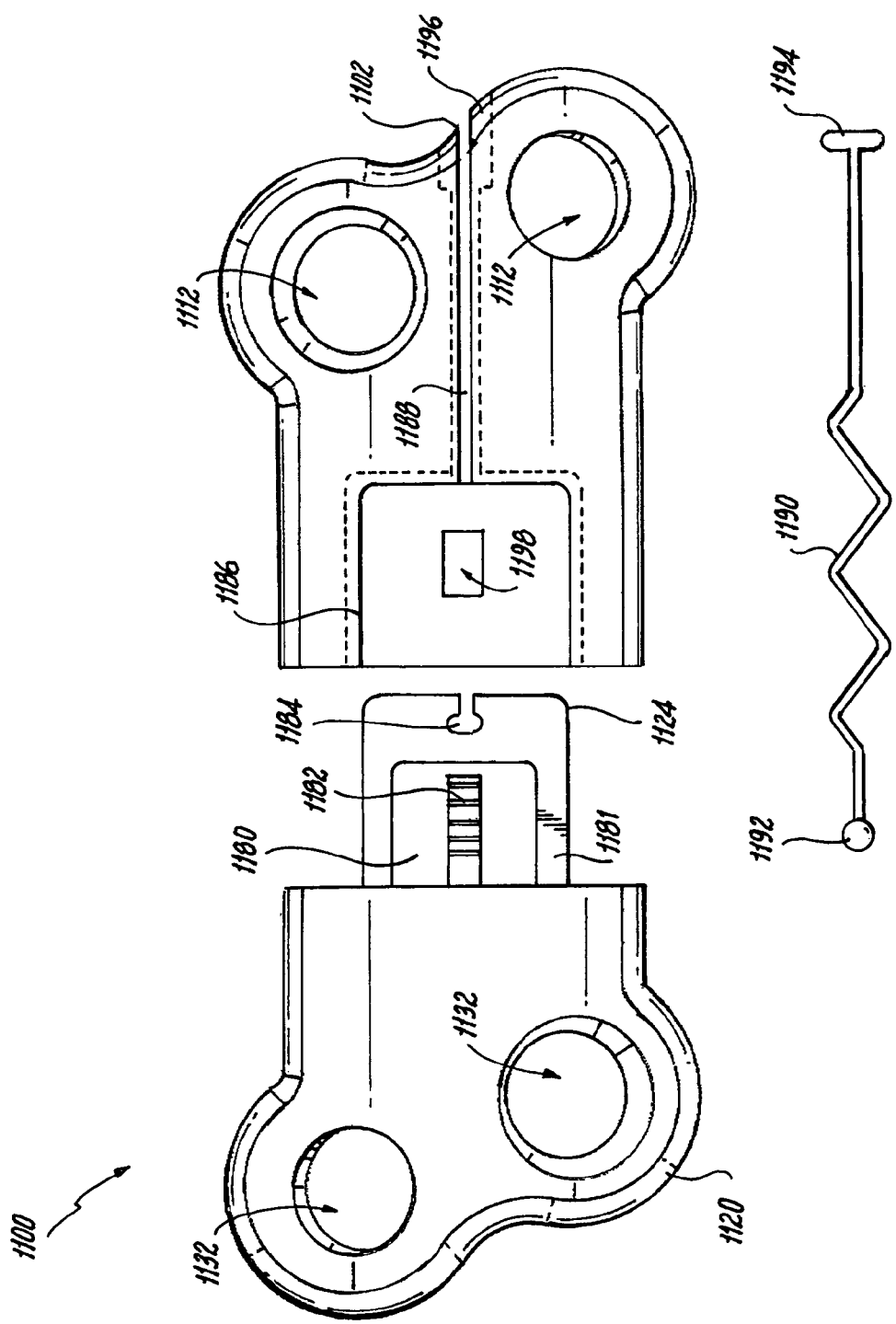
FIG. 24 is an exploded view of another bone plate assembly in accordance with the subject technology.

FIG. 24 is an exploded view of another bone plate assembly 1100 in accordance with the subject technology. The male plate portion 1120 of the bone plate assembly 1100 has an engagement member 1181 with a central flexible tab 1180 with ratchet teeth 1182 thereon. The male plate portion 1120 also defines a distal cavity 1184 in the engagement member 1181. The female plate portion 1102 defines a hollow 1186 (shown in phantom line), or a dovetail as the case may be, that snugly receives the engagement member 1181. A passage 1188 through the female plate portion 1102 allows a linear spring 1190 to extend through the female plate portion 1102 so that a head 1192 of the linear spring 1190 is captured in the cavity 1184. Another end of the spring 1194 is enlarged to be captured in a hollow 1196 of the female plate portion 1102. Thus, when assembled, the linear spring 1190 will urge the plate portions 1102, 1120 together. The female plate portion 1102 forms a window 1198 so that the ratchet teeth 1182 couple thereto for preventing the plate portions 1102, 1120 from separation unless the flexible tab 1180 is pushed downward.

Figure 25:
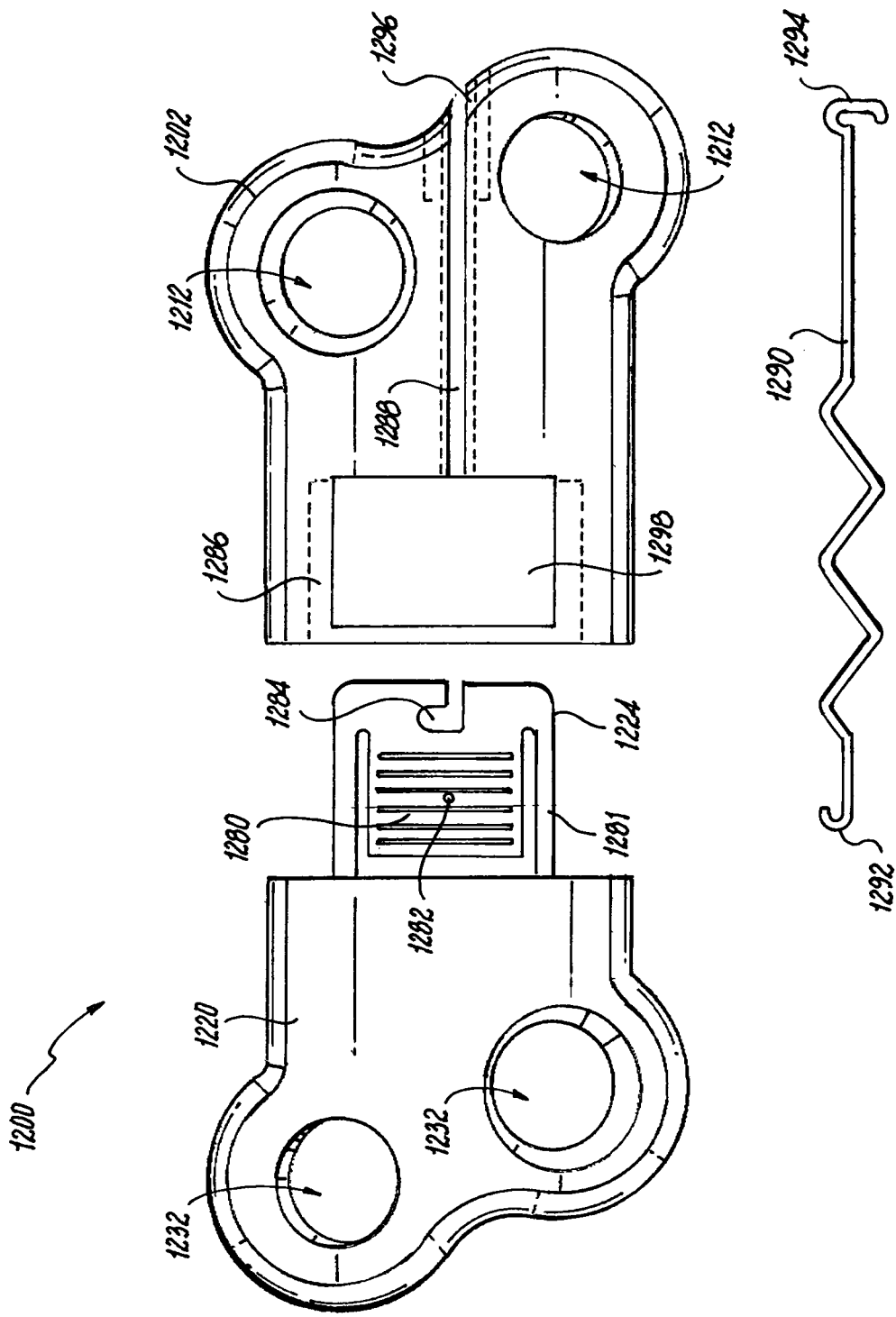
FIG. 25 is an exploded view of another bone plate assembly in accordance with the subject technology.

FIG. 25 is an exploded view of still another bone plate assembly 1200 in accordance with the subject technology. The bone plate assembly 1200 is quite similar to the bone plate assembly 1100 except that the flexible tab 1280, spring 1290, cavity 1284 and hollow 1188 are reconfigured. Hence, like reference numerals are used to indicate like elements whenever possible as has been conventional throughout this description.

Figure 26:
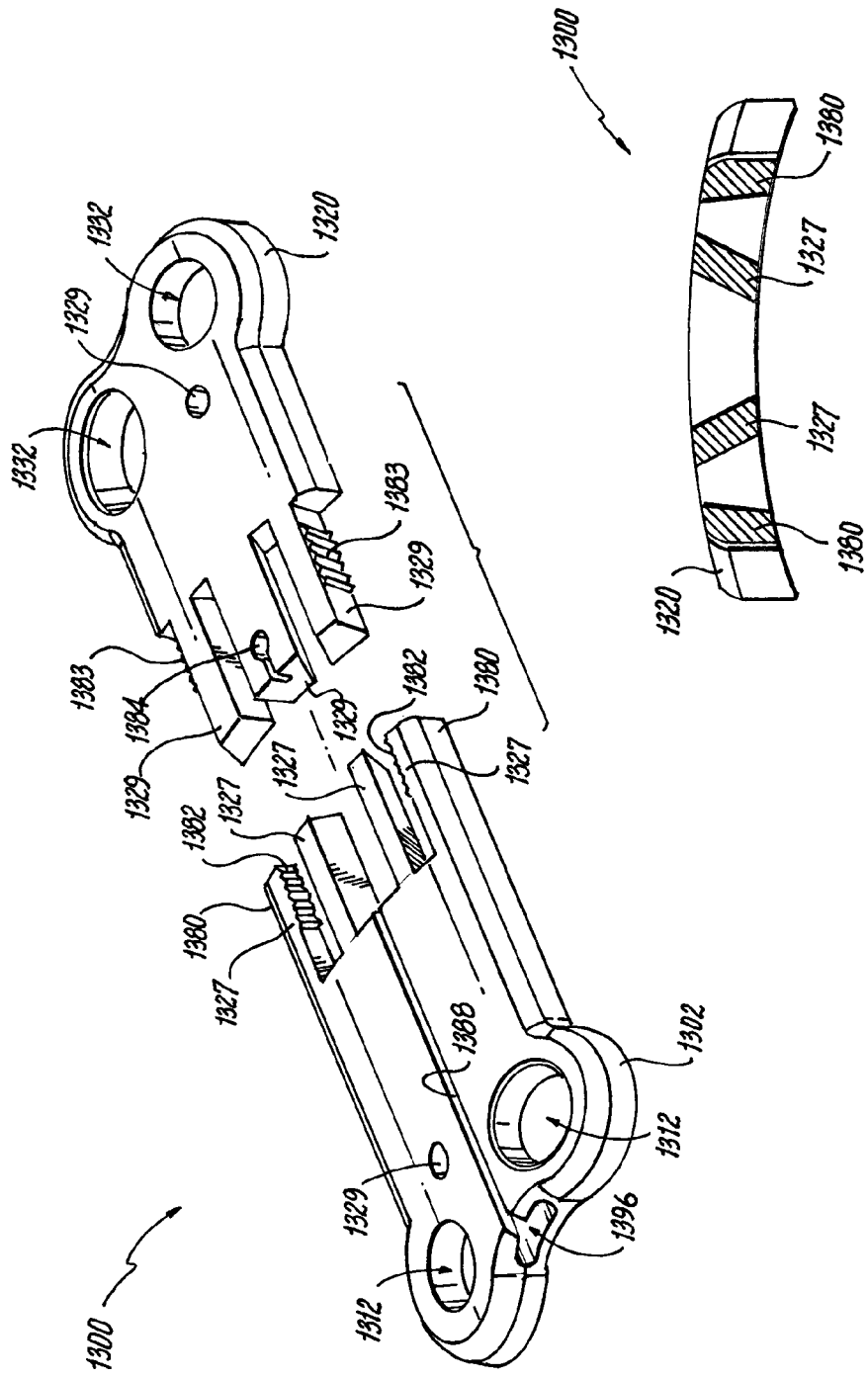
FIG. 26 is an exploded view of another bone plate assembly in accordance with the subject technology.

FIG. 26 is an exploded view of another bone plate assembly 1300 in accordance with the subject technology and FIG. 26A is a cross-sectional view of the bone plate assembly 1300. The bone plate assembly 1300 has a male plate portion 1320 and a female plate portion 1302, each of which forms several dovetail fingers 1327, 1329 that, when interlocked, only allow linear travel of the plate portions 1302, 1320. The outer fingers 1327 of the female plate portion 1302 and the outer fingers 1329 of the male plate portion 1320 include ratchet teeth 1382, 1383 that interact to deter the plates 1302, 1320 separating once engaged. Preferably, the outer fingers 1327 are sized and configured to deflect or flex to facilitate smooth operation of the ratchet mechanism.

Figure 27:
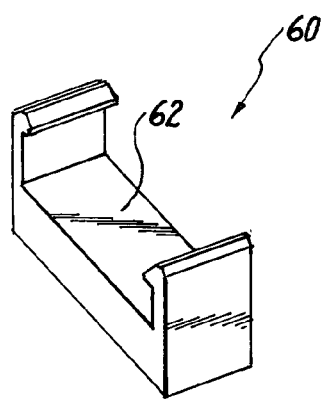
FIG. 27 is a perspective view of a modular wedge for use with a bone plate assembly.
Figure 28:
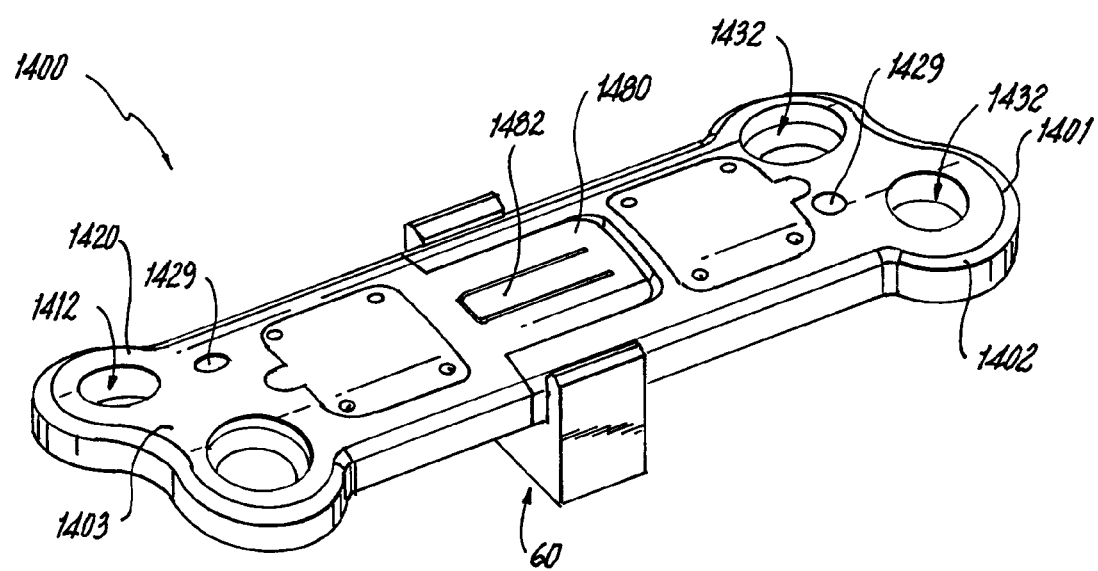
FIG. 28 is a perspective view of the modular wedge of FIG. 27 on a bone plate assembly in accordance with the subject technology.

FIG. 27 is a perspective view of a modular wedge 60 for use with a bone plate assembly (shown in FIG. 28). The modular wedge 60 is dimensioned and configured to operatively engage an outer profile of at least one of the plate portions to act as a spacer. The modular wedge 60 may be formed from a metal material, a biologic material, titanium, bone, PEEK, combinations thereof and the like.

Referring now to FIG. 28, a perspective view of the modular wedge 60 on a bone plate assembly 1400 is shown. The bone plate assembly 1400 is shown in the closed position as it would be with the modular wedge 60 in place after final placement to provide separation and support between the ends 1401, 1403 of the bone plate assembly 1400.

Figure 29:
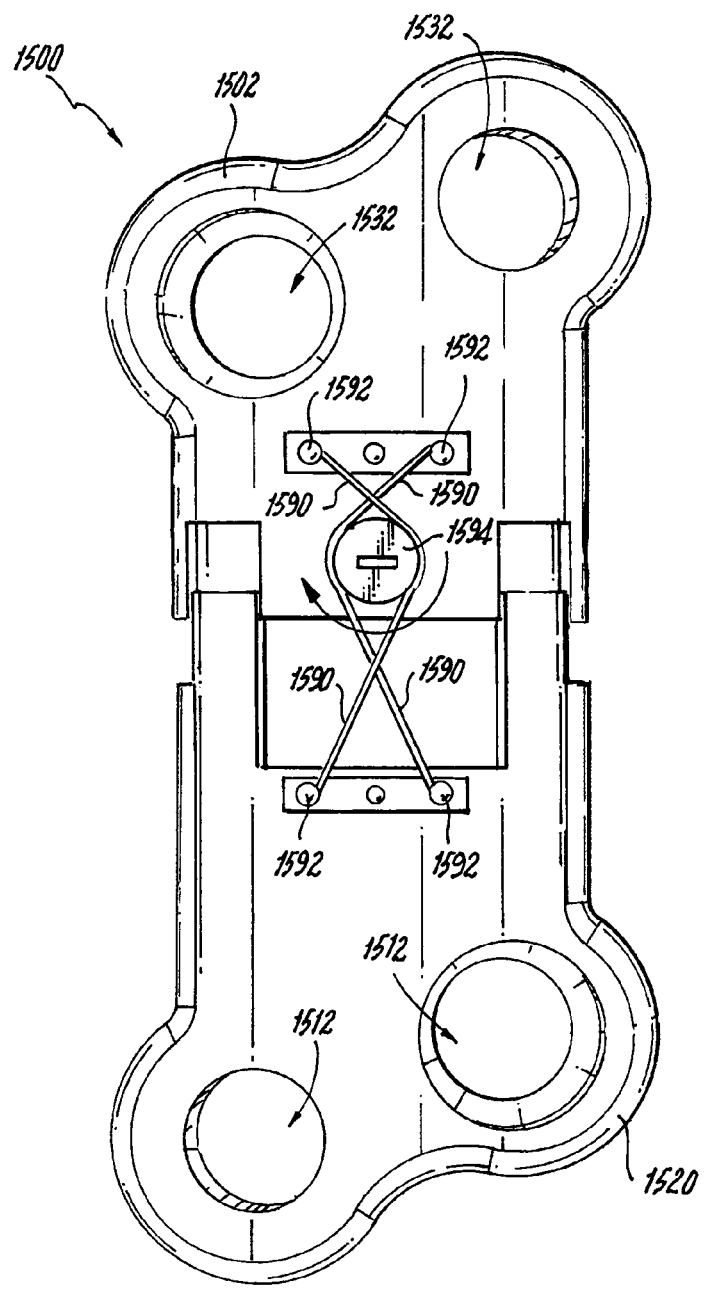
FIG. 29 is a top view of another bone fracture plate assembly in accordance with the subject technology.

Referring now to FIG. 29, another bone plate assembly 1500 is shown. The bone plate assembly 1500 includes wires 1590 extending between hubs 1592 located on each plate portion 1502, 1520. The wires 1590 connect to one of the plate segments 1502, 1520 and a spool 1594 which is free to rotate. When the spool 1594 is rotated, the wires 1592 wrap around the spool 1594 thereby shortening the wire length and pulling the plate segments 1502, 1520 inward. Preferably, multiple wires 1590 are used. Also, the spool 1594 may be made with ratchet teeth to selectively rotate in one direction and, in turn, the wires 1590 could be tightened before implantation, thereby creating a pre-load.

As can be seen upon review of the subject disclosure, selection of the configuration of the spring largely determines the compression force. Different cross-sections and angle combinations at the flex points of the spring result in different compression forces. Table 1 below illustrates some exemplary data for various configuration springs of a U-shape as drawn in FIG. 15. The cross-section is taken at the flex points (reference numeral 481 as seen in FIG. 15) and the springs are 0.5 mm thick. The angle would be the inner angle between the extending ears. Typically, the resulting force is about 9-10 lbs.

TABLE 1

| CROSS-SECTION | ANGLE | F (lbs.) | F (N) | Spread (mm) |
|---|---|---|---|---|
| 1.40 mm | 95 | 8.6 | 38.184 | 2.08 |
| 1.40 mm | 105 | 11.8 | 52.392 | 2.08 |
| 1.50 mm | 95 | 11.8 | 52.392 | 2.18 |
| 1.30 mm | 95 | 8.8 | 39.072 | 2.15 |
| 1.30 mm | 105 | 11.8 | 52.392 | 2.18 |
| 1.35 mm | 95 | 8.8 | 39.072 | 2.21 |

The springs were fabricated from nitinol. A preferred cross-section and angle combination will be approximately 1.36-1.40 mm and 97-100°, respectively. The springs are designed so that compression is maintained even when the plates have fully closed.

The bone plates and systems of the subject technology would be advantageous to provide support and/or stabilization and/or compression in a wide variety of applications. For example, without limitation, the subject technology is useful in applications related to the clavicle, humerus, jaw bone, ulna, radius, hand (1-5 metacarpal), rib, scapula, parts of the lower body such as the femur, tibia, fibula, pelvis, and parts of the foot or ankle such as the calcaneus, metatarsal bones, talus and cuboid among many other possibilities. The subject technology is particularly useful to stabilize the spine after, for example, a spinal procedure like disk removal.

While the subject invention has been shown and described with reference to preferred embodiments of dynamic bone fracture plates, those skilled in the art will readily appreciate that various changes and/or modifications may be made thereto without departing from the spirit and scope of the subject invention as defined by the appended claims. For example, each claim may depend from any or all claims, even in a multiple dependent manner, even though such has not been originally claimed.

What is claimed is:

1. A bone plate assembly comprising:
a female plate portion having: a post upstanding from the female plate portion; a first end; a second end defining two apertures for fasteners; and an arm extending from the first end parallel to the female plate portion, the arm defining a plurality of ratchet teeth;
a male plate portion having: two posts upstanding from the male plate portion; a first end for coupling to the first end of the female plate portion so that the plate portions only move linearly with respect to each other and a slot for receiving the arm; a second end defining two apertures for fasteners; and a pawl for engaging the ratchet teeth; and
a spring for dynamically connecting the plate portions by applying a compressive load therebetween, the spring having: an apex portion defining a hole for coupling to the post of the female plate portion; and a pair of elongated ears extending from the apex portion, each ear defining a slot for coupling to the posts of the male plate portion, respectively,
wherein, the first end of the male plate inserts in the first end of the female plate so that the arm extends into the slot of the male plate portion and the ratchet teeth are engaged by the pawl to retain the plate portions together, and the spring mounts on the posts of the plate portions such that the spring biases the male and female plate portions together.

2. A bone plate assembly as recited in claim 1, wherein the arm includes a first tooth on a distal end and the plurality of ratchet teeth are linearly spaced from the first tooth and the male plate portion includes a second pawl for selectively engaging the first tooth in an open position in which the male and female plate portions are held apart.

3. A bone plate assembly as recited in claim 2, wherein the arm is deflectable so that the first tooth can be disengaged from the second pawl.

4. A bone plate assembly as recited in claim 2, further comprising a top plate coupled to the male and female plate portions for covering the spring.

5. A bone plate assembly as recited in claim 4, wherein the top plate defines a hole for allowing a user to deflect the arm to separate the first tooth from the second pawl so that the spring dynamically biases the male and female plate together.

6. A bone plate assembly comprising:
a) at least first and second plate segments adapted and configured for movement relative to one another from a spaced apart position and an approximated position;
b) ratchet means for allowing the first and second plate segments to move to the approximated position while preventing the first and second plate segments from moving toward a spaced apart position; and
c) a spring mechanism extending between the at least first and second plate segments to bias the at least first and second plate segments together, wherein the spring mechanism includes: an apex defining a hole for coupling to one of the plate segments; and a pair of elongated ears extend from the apex, each ear defining a slot for slidingly coupling to posts on the other plate portion, respectively, such that the elongated ears create a compression force between the plate portions that generally biases the plate portions together.

7. A bone plate assembly as recited in claim 6, wherein the ratchet means includes a ratcheting pawl member operatively associated with the first plate segment and a rack of ratchet teeth provided on the second plate segment for interacting with the pawl member.

8. A bone plate assembly as recited in claim 6, further comprising at least one bar coupled between the at least first and second plate segments in a sliding arrangement to act as a linear guide.

9. A bone plate assembly as recited in claim 8, wherein the at least one bar and sliding arrangement is a male dovetail portion on the first plate segment and a complimentary female dovetail portion on the second plate segment.

10. A bone plate assembly as recited in claim 6, further comprising:
   d) a locking mechanism to lock for selectively setting a gap between the at least first and second plate segments to create a static open position and unlock to create a dynamic closed position in which the spring mechanism can draw the at least first and second plate segments together.

11. A bone plate assembly as recited in claim 6, further comprising a top plate coupled to the plate portions for covering the spring mechanism, wherein the top plate defines a hole for allowing a surgeon disengage the ratchet means.

12. A bone plate assembly as recited in claim 6, wherein the spring is fabricated from a memory alloy and rotationally fixed.

13. A bone plate assembly for facilitating healing of a bone fracture comprising:

a first plate portion;

a second plate portion coupled to the first plate portion so that the plates move with respect to each other linearly; and a spring tensioning mechanism for dynamically connecting the first and second plate portions such that when mounted on opposite sides of a bone fracture, the first and second plate portions apply a compressive load to the bone fracture, wherein the spring mechanism includes: an apex defining a hole for coupling to one of the plate segments; and a pair of elongated ears extend from the apex, each ear defining a slot for slidingly coupling to posts on the other plate portion, respectively, such that the elongated ears create a compression force between the plate portions that generally biases the plate portions together.

* * * * *